(12) United States Patent
Bolduan et al.

(10) Patent No.: US 12,102,048 B2
(45) Date of Patent: Oct. 1, 2024

(54) GENERATION OF HAPLOID PLANTS

(71) Applicant: KWS SAAT SE & CO. KGAA, Einbeck (DE)

(72) Inventors: Christof Bolduan, Einbeck (DE); Frank Breuer, Einbeck (DE); Monika Kloiber-Maitz, Einbeck (DE); Markus Niessen, Laatzen (DE); Milena Ouzunova, Göttingen (DE); Britta Schulz, Einbeck (DE); Silke Wieckhorst, Einbeck (DE)

(73) Assignee: KWS SAAT SE & CO. KGAA, Einbeck (DE)

( * ) Notice: Subject to any disclaimer, the term of this patent is extended or adjusted under 35 U.S.C. 154(b) by 798 days.

(21) Appl. No.: 17/068,487

(22) Filed: Oct. 12, 2020

(65) Prior Publication Data

US 2021/0079419 A1 Mar. 18, 2021

Related U.S. Application Data

(62) Division of application No. 15/539,065, filed as application No. PCT/EP2015/081158 on Dec. 23, 2015, now Pat. No. 10,844,401.

(30) Foreign Application Priority Data

Dec. 23, 2014 (EP) .................................. 14004389

(51) Int. Cl.
| | | |
|---|---|---|
| *A01H 1/08* | (2006.01) | |
| *A01H 1/02* | (2006.01) | |
| *A01H 5/06* | (2018.01) | |
| *A01H 5/10* | (2018.01) | |
| *A01H 6/20* | (2018.01) | |
| *C07K 14/415* | (2006.01) | |
| *C12N 15/82* | (2006.01) | |

(52) U.S. Cl.
CPC .............. *A01H 1/08* (2013.01); *A01H 1/021* (2021.01); *A01H 1/023* (2021.01); *A01H 5/06* (2013.01); *A01H 5/10* (2013.01); *A01H 6/20* (2018.05); *C07K 14/415* (2013.01); *C12N 15/8287* (2013.01)

(58) Field of Classification Search
CPC .............. A01H 1/08; A01H 6/20; A01H 5/06; C12N 15/8287
See application file for complete search history.

(56) References Cited

U.S. PATENT DOCUMENTS

| | | |
|---|---|---|
| 2011/0083202 A1 | 4/2011 | Chan et al. |
| 2014/0090099 A1 | 3/2014 | Chan et al. |
| 2017/0280646 A1 | 10/2017 | Houben et al. |

FOREIGN PATENT DOCUMENTS

| | | |
|---|---|---|
| WO | 2011/044132 A1 | 4/2011 |
| WO | 2014/110274 A2 | 7/2014 |
| WO | 2016/030019 A1 | 3/2016 |
| WO | 2016/138021 A1 | 9/2016 |

OTHER PUBLICATIONS

Ravi, M. and Chan, S. Nature (Mar. 2010) vol. 464; No. 7288; pp. 615-620. (Year: 2010).*
Ravi et al., "Haploid Plants Produced by Centromere-Mediated Genome Elimination", Nature 464 (Mar. 25, 2010): 615-619. (Year: 2010).*
Chomczynski, P. et al., "Single-Step Method of RNA Isolation by Acid Guanidinium Thiocyanate-Phenol-Chloroform Extraction", Analytical Biochemistry (1987), vol. 162, pp. 156-159.
Clough, S.J. et al., "Floral dip: a simplified method for Agrobacterium-mediated transformation of *Arabidopsis thaliana*", The Plant Journal (1988), vol. 16(6), pp. 735-743.
Edwards, K. et al., "A simple and rapid method for the preparation of plant genomic DNA for PCR analysis", Nucleic Acids Research (1991), vol. 19, No. 6, p. 1349.
Galbraith, D.W. et al., "Rapid Flow Cytometric Analysis of the Cell Cycle in Intact Plant Tissues", Science (1983), vol. 220(4601 ), pp. 1049-1051. [doi: 10.1126/science.220.4601.1049].
Gottwald, Sven et al., "Tilling in the two-rowed barley cultivar 'Berke' revieals preferred sites of functional diversity in the gene HvHox!", BMC Research Notes (2009). vol. 2(258) pp. 1-14.
International Search Report and Written Opinion dated Dec. 18, 2015 issued in the International Application No. PCT/EP2015/001752.
Kasha and Kao, Nature vol. 225; Feb. 28, 1970 pp. 874-876 (Year: 1970).
Lermontova, I. et al. "Knockdown of CENH3 in *Arabidopsis* reduces mitotic divisions and causes sterility by distributed melotic chromosome segregation", The Plant Journal (2011 ). vol. 68, pp. 40-50.[doi: 10.1111/J.1365-313X.2011.04664/X].
Lindsey, K. et al., "Transformation of Sugarbeet (*Beta vullgaris*) by Agrobacterium tumefaciens". Journal of Experimental Botany (1990), vol. 41, No. 226, pp. 529-536.
Neuffer. M.G. et al., "Mutants of Maize", Cold Spring Harbor Laboratory Press, New York (1997), 468 pages, ISBN 0-87969-444-0. (see attached review).
Rost, B. et al., "Combining Evolutionary Information and Neural Networks to Predict Protein Secondary Structure", Proteins: Structure, Function, and Genetics (1994), vol. 19, pp. 55-72.
Rost, B. et al., "Conservation and Prediction of Solvent Accessibility in Protein Families", Proteins: Structure, function, Genetics (1994), vol. 20, pp. 216-226.

(Continued)

*Primary Examiner* — Russell Kallis
(74) *Attorney, Agent, or Firm* — Troutman Pepper Hamilton Sanders LLP

(57) ABSTRACT

The present invention relates to non-transgenic and transgenic plants, preferably crop plants, having biological activity of a haploid inducer and comprising a polynucleotide which comprises a nucleotide sequence encoding a centromer histone H3 (CENH3) protein, wherein the polynucleotide comprises at least one mutation causing an alteration of the amino acid sequence of the CENH3 protein, and to a part of the part. Further, the invention provides methods of generating the inducer plants, methods of generating haploid and double haploid plants using the inducer plants as well as methods of facilitating cytoplasm exchange.

11 Claims, 1 Drawing Sheet

Specification includes a Sequence Listing.

(56) References Cited

OTHER PUBLICATIONS

Rost, B. et al., "Transmembrane helices predicted at 95% accuracy", Protein Science (1995), vol. 4, pp. 521-533.
Sanei, M. et al., "Loss of centromeric histone H3 (CENH3) from centromeres precedes uniparental chromosome elimination in interspecific barley hybrids", PNAS (2011), vol. 108(33), pp. E498-E505. [www.pnas.orgicgildol/10.10731 pnas, 11031901081].
Sanel, M. et al. PNAS, Aug. 16, 2011, 1-15 pp. (Year: 2011).
Bhatnagar-Mathur, Pooja et al., "Engineering Centromers for Haploidy Induction in Grain Legumes", ICRISAT Asia Regional Planning Meeting (2014), XP055193834.
Comai, L., "Genome Elimination: Translating Basic Research into a Future Tool for Plant Breeding", PLoS Biol. (2014), vol. 12, No. 6, e1001876.
European Partial Search Report Issued in European Patent Application No. 14004389.4, dated Jun. 12, 2015, 11 pages.
European Extended Search Report Issued in European Patent Application No. 14004389.4, dated Sep. 30, 2015, 16 pages.
International Search Report and Written Opinion Issued in PCT/EP2015/081158, dated Feb. 14, 2017, 24 pages.
Ishii, Takayoshi et al., "Functional characterization of barley CENH3 variants", Plant Molecular Cytogenetics in Genomic and Postgenomic Era (2014), XP55191331, p. 51.
Karimi-Ashtiyani, Raheleh et al., "Point mutation impairs centromeric CENH3 loading and induces haploid plants", Proceedings of The National Academy of Sciences (2015), vol. 112, No. 36, pp. 11211-11216.
Lermontova, Inna et al., "CENH3 for Establishing and Maintaining Centromeres" In: "Plant Centromere Biology", John Wiley & Sons, Oxford (2013), pp. 67-82.
Marin-Rodriguez, Brenda, "Can Point Mutations in Kinetochore Proteins Create Haploid Plants in *Arabidopsis thaliana*?", UC Davis Explorations (2014), XP55191293, 7 pages.
Moraes, Izabel C.R. et al., "Structural requirements for CENH3 targeting to centromeric chromatin", Ph.D. thesis (2011), XP55191122, pp. 53-56.
Ravi, Maruthachalam et al., "Haploid plants produced by centromere-mediated genome elimination", Nature (2010), vol. 464, No. 7288, pp. 615-620.
Ravi, Maruthachalam et al., "A haploid genetics toolbox for *Arabidopsis thaliana*", Nature Communications (2014), vol. 5, p. 5334.
Ravi, Maruthachalam et al., "Centromere-Mediated Generation of Haploid Plants", Plant Centromere Biology (2013), XP55191054, p. 169-181.
Ravi, Maruthachalam et al., "The Rapidly Evolving Centromere-Specific Histone Has Stringent Functional Requirements in *Arabidopsis thaliana*", Genetics (2010), vol. 186, No. 2, pp. 461-471.
Li et al., "Variation for Thermal Properties of Starch in Tropical Maize Germ Plasm", Cereal Chem. vol. 71, No. 1, 1994, pp. 87-90.
Chan et al., "Chromosome engineering Power tools for plant genetics", Trends in Biotechnology, Elsevier Publications, vol. 28, No. 12, Oct. 8, 2010, pp. 605-610.
Britt et al., Cenh3: An Emerging Player in Haploid Induction Technology, Frontiers in Plant Science, Apr. 12, 2016, vol. 7, Article 357, pp. 1-10.
UniprotKB—QBRVQ9, Jan. 23, 2007.
Lermontova et al., "Loading of *Arabidopsis* Centromeric Histone CENH3 Occurs Mainly during G2 and Requires the Presence of the Histone Fold Domain", The Plant Cell, vol. 18, Oct. 2006, pp. 615-618.
Evtushenko et al., "Conserved molecular structure of the centromeric histone CENH3 in Secale and its phylogenetic relationships", Scientific Reports, 2017, vol. 7: 17628, 10 pages.
Keith et al., "Analysis of Primary Structural Determinants That Distinguish the Centromere-Specific Function of Histone Variant Cse4p from Histone H3", Molecular and Cellular Biology, 1999, vol. 19, No. 9, pp. 6130-6139.
Kalinowska et al., "State-of-the-art and novel developments of in vivo haploid technologies", Theoretical and Applied Genetics, 2019, vol. 132, No. 3, pp. 593-605.
Ren et al., "Novel technologies in doubled haploid line development", Plant Biotechnology Journal, 2017, vol. 15, No. 11, pp. 1361-1370.
Jacquier et al., "Puzzling out plant reproduction by haploid induction for innovations in plant breeding", Nature Plants, 2020, vol. 6, No. 6, pp. 610-619.
Kelliher et al., "Maternal Haploids Are Preferentially Induced by CENH3-tailswap Transgenic Complementation in Maize ", Frontiers in Plant Science, 2016, vol. 7, Article 414, pp. 1-11.

\* cited by examiner

```
                           SEQUENCE LISTING

<160> NUMBER OF SEQ ID NOS: 24

<210> SEQ ID NO 1
   <211> LENGTH: 15
   <212> TYPE: PRT
   <213> ORGANISM: Artificial Sequence
   <220> FEATURE:
   <223> OTHER INFORMATION: amino acid consensus sequence of the N-terminal
         tail domain of the CENH3 (part A)
   <220> FEATURE:
   <221> NAME/KEY: misc_feature
   <222> LOCATION: (7)..(8)
   <223> OTHER INFORMATION: Xaa can be any naturally occurring amino acid

<400> SEQUENCE: 1

Met Ala Arg Thr Lys His Xaa Xaa Ala Arg Arg Ser Arg Lys Arg
   1               5                   10                  15

<210> SEQ ID NO 2
   <211> LENGTH: 14
   <212> TYPE: PRT
   <213> ORGANISM: Artificial Sequence
   <220> FEATURE:
   <223> OTHER INFORMATION: amino acid consensus sequence of the N-terminal
         tail domain of the CENH3 (part B)
   <220> FEATURE:
   <221> NAME/KEY: misc_feature
   <222> LOCATION: (6)..(6)
   <223> OTHER INFORMATION: Xaa can be any naturally occurring amino acid

<400> SEQUENCE: 2

Gln Ser Gln Thr Gln Xaa Lys Lys Lys His Arg Tyr Arg Pro
   1               5                   10

<210> SEQ ID NO 3
   <211> LENGTH: 15
   <212> TYPE: PRT
   <213> ORGANISM: Artificial Sequence
   <220> FEATURE:
   <223> OTHER INFORMATION: amino acid consensus sequence of the Alpha-N-
         helix of the CENH3
   <220> FEATURE:
   <221> NAME/KEY: misc_feature
   <222> LOCATION: (10)..(10)
   <223> OTHER INFORMATION: Xaa can be any naturally occurring amino acid

<400> SEQUENCE: 3

Gly Thr Val Ala Leu Arg Glu Ile Arg Xaa Phe Gln Lys Thr Thr
   1               5                   10                  15

<210> SEQ ID NO 4
   <211> LENGTH: 11
   <212> TYPE: PRT
   <213> ORGANISM: Artificial Sequence
   <220> FEATURE:
   <223> OTHER INFORMATION: amino acid consensus sequence of the Alpha-1-
         helix of the CENH3
```

```
<400> SEQUENCE: 4

Ala Ala Pro Phe Ile Arg Leu Val Arg Glu Ile
1               5                   10

<210> SEQ ID NO 5
<211> LENGTH: 13
<212> TYPE: PRT
<213> ORGANISM: Artificial Sequence
<220> FEATURE:
<223> OTHER INFORMATION: amino acid consensus sequence of the loop1 of
      the CENH3
<220> FEATURE:
<221> NAME/KEY: misc_feature
<222> LOCATION: (7)..(7)
<223> OTHER INFORMATION: Xaa can be any naturally occurring amino acid

<400> SEQUENCE: 5

Thr Asn Phe Leu Ala Pro Xaa Glu Val Thr Arg Trp Thr
1               5                   10

<210> SEQ ID NO 6
<211> LENGTH: 29
<212> TYPE: PRT
<213> ORGANISM: Artificial Sequence
<220> FEATURE:
<223> OTHER INFORMATION: amino acid consensus sequence of the Alpha-2-
      helix of the CENH3

<400> SEQUENCE: 6

Ala Glu Ala Leu Leu Ala Leu Gln Glu Ala Ala Glu Asp Phe Leu Val
1               5                   10                  15

His Leu Phe Glu Asp Ala Met Leu Cys Ala Ile His Ala
            20                  25

<210> SEQ ID NO 7
<211> LENGTH: 7
<212> TYPE: PRT
<213> ORGANISM: Artificial Sequence
<220> FEATURE:
<223> OTHER INFORMATION: amino acid consensus sequence of the loop2 of
      the CENH3

<400> SEQUENCE: 7

Lys Arg Val Thr Leu Met Lys
1               5

<210> SEQ ID NO 8
<211> LENGTH: 10
<212> TYPE: PRT
<213> ORGANISM: Artificial Sequence
<220> FEATURE:
<223> OTHER INFORMATION: amino acid consensus sequence of the Alpha-3-
      helix of the CENH3

<400> SEQUENCE: 8

Lys Asp Phe Glu Leu Ala Arg Arg Leu Gly
1               5                   10

<210> SEQ ID NO 9
<211> LENGTH: 6
<212> TYPE: PRT
<213> ORGANISM: Artificial Sequence
<220> FEATURE:
<223> OTHER INFORMATION: amino acid consensus sequence of the C-terminal
      domain of the CENH3
```

<400> SEQUENCE: 9

Gly Lys Gly Arg Pro Trp
1               5

<210> SEQ ID NO 10
<211> LENGTH: 537
<212> TYPE: DNA
<213> ORGANISM: Artificial Sequence
<220> FEATURE:
<223> OTHER INFORMATION: Arabidopsis thaliana - cDNA coding for CENH3

<400> SEQUENCE: 10

```
atggcgagaa ccaagcatcg cgttaccagg tcacaacctc ggaatcaaac tgatgccgcc    60
ggtgcttcat cttctcaggc ggcaggtcca actacgaccc cgacaaggag aggcggtgaa   120
ggtggagata atactcaaca acaaatcct acaacttcac cagctactgg tacaaggaga   180
ggggctaaga gatccagaca ggctatgcca cgaggctcac agaagaagtc ttatcgatac   240
aggccaggaa ccgttgctct aaaagagatt cgccatttcc agaagcagac aaaccttctt   300
attccggctg ccagtttcat aagagaagtg agaagtataa cccatatgtt ggcccctccc   360
caaatcaatc gttggacagc tgaagctctt gttgctcttc aagaggcggc agaagattac   420
ttggttggtt tgttctcaga ttcaatgctc tgtgctatcc atgcaagacg tgttactcta   480
atgagaaaag actttgaact tgcacgccgg cttggaggaa aaggcagacc atggtga      537
```

<210> SEQ ID NO 11
<211> LENGTH: 178
<212> TYPE: PRT
<213> ORGANISM: Arabidopsis thaliana

<400> SEQUENCE: 11

Met Ala Arg Thr Lys His Arg Val Thr Arg Ser Gln Pro Arg Asn Gln
1               5                   10                  15

Thr Asp Ala Ala Gly Ala Ser Ser Gln Ala Ala Gly Pro Thr Thr
            20                  25                  30

Thr Pro Thr Arg Arg Gly Gly Glu Gly Gly Asp Asn Thr Gln Gln Thr
        35                  40                  45

Asn Pro Thr Thr Ser Pro Ala Thr Gly Thr Arg Gly Ala Lys Arg
    50                  55                  60

Ser Arg Gln Ala Met Pro Arg Gly Ser Gln Lys Lys Ser Tyr Arg Tyr
65                  70                  75                  80

Arg Pro Gly Thr Val Ala Leu Lys Glu Ile Arg His Phe Gln Lys Gln
                85                  90                  95

Thr Asn Leu Leu Ile Pro Ala Ala Ser Phe Ile Arg Glu Val Arg Ser
            100                 105                 110

Ile Thr His Met Leu Ala Pro Pro Gln Ile Asn Arg Trp Thr Ala Glu
        115                 120                 125

Ala Leu Val Ala Leu Gln Glu Ala Ala Glu Asp Tyr Leu Val Gly Leu
    130                 135                 140

Phe Ser Asp Ser Met Leu Cys Ala Ile His Ala Arg Arg Val Thr Leu
145                 150                 155                 160

Met Arg Lys Asp Phe Glu Leu Ala Arg Arg Leu Gly Gly Lys Gly Arg
                165                 170                 175

Pro Trp

<210> SEQ ID NO 12

```
<211> LENGTH: 4001
<212> TYPE: DNA
<213> ORGANISM: Brassica napus
<220> FEATURE:
<221> NAME/KEY: Intron
<222> LOCATION: (1892)..(1972)
<220> FEATURE:
<221> NAME/KEY: Intron
<222> LOCATION: (2020)..(2104)
<220> FEATURE:
<221> NAME/KEY: Intron
<222> LOCATION: (2148)..(2208)
<220> FEATURE:
<221> NAME/KEY: Intron
<222> LOCATION: (2264)..(2358)
<220> FEATURE:
<221> NAME/KEY: Intron
<222> LOCATION: (2399)..(2507)
<220> FEATURE:
<221> NAME/KEY: Intron
<222> LOCATION: (2624)..(2755)
<220> FEATURE:
<221> NAME/KEY: Intron
<222> LOCATION: (2832)..(2933)
<220> FEATURE:
<221> NAME/KEY: Intron
<222> LOCATION: (3012)..(3091)

<400> SEQUENCE: 12
tgtccgggag gatccaccgg cggtggtcgt tactccattt taacttgatg tcttgaaagc      60
agaggacatg gtatggtggc ggcagaatct attttttagtt gttaattttt cttttcctct    120
gattcttttt attttttttcg aatgaactaa ctttgggttt attcagaaga attatcatct    180
aaaaactgat tcaataaaca aaataattta catatttcac aatgagccat tagtaaacaa    240
gtcgaaagtg aaaccaaatg ggaagagaac aattttaata aaaatatgtt ctaatttcct    300 acttttttatg aattgaactc ccgaagagaa tggccgaaga acggagtaaa agctcaatga    360
ttgtaaaagc tatgtattct cttgctttga ggaaaaagct ttttgtttgc actcataggc    420
ctgatatgtt gtgatggctc tttacatatt gggtcttttg tggtctatta aacgttact     480 gaagaattag tttatcgcat ttaaaaaaaa atatttgaaa accacatatc taaaatctca    540
atatattatt tattgataga tgaaaagaaa aatagtttat aaaataatat taattggtaa    600
atggaagtca aaattttaca tttaatacat gactagttcg attctccggc tgaaacccat    660
ttaccactga gccaagacca cttgattata tatatcaagc tcttgttttt tgcattaaca    720
aaagttgcat ccaaaatttc aaaacaacaa ctaaattaat gtctttctat tttcaaagtt    780
ttatctccaa acctattaat agtttaattt tttttttttaa aattaggaaa ccggttaaaa    840 tatatttttaa atacaaaaaa cttaaacaat gaatcattta tttatttatt cttcaaaatt    900
taaatatccg aacccggccc aaaatatccg aacccgaaca taaatatccg aacccgact    960 cgaagtgtag aaaatatccg aacgggtttt ataccttttat actgaaatac cctatacgaa   1020
cccgaatgtg tatccgaacg cccccctacaa tatatgatca tcatttgtat cttgattgaa   1080
caaaaaaaaa gttaaactat tgatcacaaa atttttcaatg tgagactttt accatttta    1140 gtcatttata gtcgttttta aaaattcaaa atataactta taagaaaaaa tctaattttt    1200
tttattatat gcttaatgtg attgtttaat ttctttttaat aatataaaat taaacaaaaa   1260
atgagaggtt aaaaaaattg ttatcaaata tgtattattc ataatcatta attgtcatat    1320
atatgttaat tatattaggt aatttcgtag ttttttattta agaaaagaaa aaatatattt   1380
tttgtacact actaattaat ttgatagtta gtttaataaa aatatatta tattattata    1440 tggaccaact tattttttcta aaaaaaaacc actgttttaa aaaccaaacc aactataaac   1500
```

```
cggagatata ccggattgag tggctaaaac actctttgta tatatgtgct gagcaaaccc    1560
tctgagtgag atggcgtgtt aagaagtagg aggaccattc atgcctctta tgagttgtag    1620
tctgtgtgta caaaaaagaa gcgttggtgt gaaagaaagc agaaggattt gaaaatcaaa    1680
aaaattgaag gagaagcggg aaaacaaata atctctccct ccgctttttt ttctccaaat    1740
aatcaatctc tcatttcatt tgttaaccca agttttttgat aattatttca aggggttta    1800 tttatctttt attcctccgg cggcagtaag tagtaatcaa tggcgagaac caaacatttc    1860
gcttccaggg cacgagatcg caatcgaact agttagtact ctctctctct ctgcctttttt   1920 tttgatattt attttctagg ttaaaccctaa atttggcatc tgaaatttgt agatgcgact    1980
gcttcatctt cggcggcggc ggcggaaggt ccgagtgcgg tacgtcatct attttctttt    2040
cccgttttag gttttacgc aaatctcgtt actgtttttt tgacgaatcg attgaaatgt     2100
gtagaccccg acgagaagag aaggcagcca aggagaagct caacagagtg agtctttcta    2160
tttcattttc tgagatccat gaatcctttt catctctcgt gtgttgtgac atgaatcaat    2220
tgcagcagca actcctacta cgactccacc agccggtaga aaagtaagtt acatttccat    2280
ttcacaccat tcatttgctt ctttatcaac aaactgctct ctcatctgtt ttttttgttt    2340
tgttttggtt ttgtgaagaa aggagggact aagcgaacta aacaagctat gcctaaaagt    2400
tagtgacaga ttttaaaatc tctattttgg atcatcattc tctcaggaca tgtctatttg    2460
catttgttct tattatgtct gtctgtctgt ctttgtcccc cttgtaggtt ccaacaagaa    2520
gaagacattc cgttacaagc ctggaaccgt tgccctcaga gagattcgcc atttccagaa    2580
gaccaccaaa cttcttatcc ctgccgctag tttcatccga gaagttagta atgaactttg    2640
ttattcatac attcccgctt acttgttttc aatgactctg caattactga tatagaattt    2700
ggagcaacca ttatggggtg atttctctaa ctacaaatta ctaatactat cccaggtgag    2760
aagtgtcacc cagatctttg cccctcccga tgttacccgt tggactgctg aagctcttat    2820
ggctattcaa gaggtacgtg tactccttcc ctcttttgtt tcctattttc cacttgatgt    2880
ctaatttaaa ctgatcgttt tttttttata tttcttttgg tgtggggcgg ggcaggcggc    2940
tgaagatttt ttaattggct tgttctctga tgctatgctt tgcgctatcc atgcaaggcg    3000
tgttactcta agtaagtagt actccccaaa ataaggaaac ccattttata tacaacattg    3060
cctcatccat gtctgcttct cttcatatca gtgagaaaag attttgagct tgcacgccgt    3120
cttggaggaa aaggcagacc attgtgatcg tttcgcaggt tgtataactt tgttcactcc    3180
ttatgtcttg tcatttgtga tctgactgac actttctttt gaaacataac tgcttgattc    3240
aatatctagg ctgtaaaact tatcctcct tgtttactat cttatatgct ttttccttgg     3300
aattgatagt ttccattgag atttcacttg cacgaaacat atctgctttc tcaatatctc    3360
tcagtcttag aaagggctat tgactaaaag aaaagaaaat ttagaggaag atttgtaaag    3420
acatgtgttt agagagggct taattaaaaa cacacgcttc tgctagcctt gctatttgat    3480
tcccaatttc aacttttttc gaggcatatt ataaagtttt taaatgtact tggcacttca    3540
acttttataa tttatataac gattttattc taatagagca tttgtgattt catagtgttg    3600
tcatgaaact caagtaattc acaccgtccg atgttgctat tgtctaataa aatgttgaaa    3660
aaattgtcaa aacagaacaa aaaacaacat agttgtctct atggtataaa actatcacta    3720
agttgtctct atagtataat attttctcgca atcccaaaac taattttttct ttaatcaaat   3780 taaacataaa ctaaaaccat ttttaaaaag tttaatggaa aaagataaaa aaataaggta    3840
```

```
atctcgtaat gttttaaaaa ggaaaaaaaa tgtaaaaaca atttaaaaaa aagaacacac    3900
gacacagatc aaaatatca tgtaatctaa ttgcatttgg tttctaaaat cttccaaaac    3960
tattctttta aaattctcta aggtaaaact tgattccaat a                       4001
```

<210> SEQ ID NO 13
<211> LENGTH: 540
<212> TYPE: DNA
<213> ORGANISM: Artificial Sequence
<220> FEATURE:
<223> OTHER INFORMATION: Brassica napus - cDNA coding for CENH3

<400> SEQUENCE: 13

```
atggcgagaa ccaaacattt cgcttccagg gcacgagatc gcaatcgaac taatgcgact     60
gcttcatctt cggcggcggc ggcggaaggt ccgagtgcga ccccgacgag aagagaaggc    120
agccaaggag aagctcaaca gacaactcct actacgactc caccagccgg tagaaaaaaa    180
ggagggacta gcgaactaa caagctatg cctaaaagtt ccaacaagaa aagacattc     240 cgttacaagc ctggaaccgt tgccctcaga gagattcgcc atttccagaa gaccaccaaa    300
cttcttatcc ctgccgctag tttcatccga gaagtgagaa gtgtcaccca gatctttgcc    360
cctcccgatg ttacccgttg gactgctgaa gctcttatgg ctattcaaga ggcggctgaa    420 gatttttttaa ttggcttgtt ctctgatgct atgctttgcg ctatccatgc aaggcgtgtt    480
actctaatga gaaagacttt tgagcttgca cgccgtcttg gaggaaaagg cagaccattg    540
```

<210> SEQ ID NO 14
<211> LENGTH: 180
<212> TYPE: PRT
<213> ORGANISM: Brassica napus

<400> SEQUENCE: 14

```
Met Ala Arg Thr Lys His Phe Ala Ser Arg Ala Arg Asp Arg Asn Arg
1               5                   10                  15

Thr Asn Ala Thr Ala Ser Ser Ser Ala Ala Ala Glu Gly Pro Ser
            20                  25                  30

Ala Thr Pro Thr Arg Arg Glu Gly Ser Gln Gly Glu Ala Gln Gln Thr
        35                  40                  45

Thr Pro Thr Thr Thr Pro Pro Ala Gly Arg Lys Lys Gly Gly Thr Lys
    50                  55                  60

Arg Thr Lys Gln Ala Met Pro Lys Ser Ser Asn Lys Lys Lys Thr Phe
65                  70                  75                  80

Arg Tyr Lys Pro Gly Thr Val Ala Leu Arg Glu Ile Arg His Phe Gln
                85                  90                  95

Lys Thr Thr Lys Leu Leu Ile Pro Ala Ala Ser Phe Ile Arg Glu Val
            100                 105                 110

Arg Ser Val Thr Gln Ile Phe Ala Pro Pro Asp Val Thr Arg Trp Thr
        115                 120                 125

Ala Glu Ala Leu Met Ala Ile Gln Glu Ala Ala Glu Asp Phe Leu Ile
    130                 135                 140

Gly Leu Phe Ser Asp Ala Met Leu Cys Ala Ile His Ala Arg Arg Val
145                 150                 155                 160

Thr Leu Met Arg Lys Asp Phe Glu Leu Ala Arg Arg Leu Gly Gly Lys
                165                 170                 175

Gly Arg Pro Leu
            180
```

```
<210> SEQ ID NO 15
<211> LENGTH: 3088
<212> TYPE: DNA
<213> ORGANISM: Sorghum bicolor
<220> FEATURE:
<221> NAME/KEY: Intron
<222> LOCATION: (377)..(487)
<220> FEATURE:
<221> NAME/KEY: Intron
<222> LOCATION: (514)..(618)
<220> FEATURE:
<221> NAME/KEY: Intron
<222> LOCATION: (662)..(1094)
<220> FEATURE:
<221> NAME/KEY: Intron
<222> LOCATION: (1217)..(1312)
<220> FEATURE:
<221> NAME/KEY: Intron
<222> LOCATION: (1391)..(2087)
<220> FEATURE:
<221> NAME/KEY: Intron
<222> LOCATION: (2164)..(2556)

<400> SEQUENCE: 15
```

| | | | | | |
|---|---|---|---|---|---|
| catctctcac | tgccatccgg | gtccactact | cccaacgttc | ggcacgccag | gtatagccgt | 60 |
| taccccggta | ggccccactg | gtacacggac | aaaggttagc | ggtcaccgcg | aatcgtgaat | 120 |
| acttgtgact | acggggtgct | aattataaaa | acgccgcaca | tcctttcgtt | tcgccatttc | 180 |
| acccccttc | ccttcccgta | gagaggaaaa | aaacccaccg | tcgacccgcc | cggccgcccg | 240 |
| agagttctga | atcgaaaccg | tcggccgcga | ccgcgagagc | agcgcggggc | gcccaccgtg | 300 |
| atggctcgaa | ccaagcacca | ggccgtgagg | aagctgccgc | agaagcccaa | gaagaagctc | 360 |
| cagttcgagc | gcgcaggtaa | gcccgcgtcc | ccgcgctgaa | ccccctccg | cctcgcgagc | 420 |
| agacgctgcc | gctgctctcc | gtcgcccctg | gtgctaagcg | cgttcctttt | ttttccttct | 480 |
| tttgcaggtg | gggcgagtac | gtcggcgacc | ccggtgagtg | cgtgcgtgcg | tgcgggaatt | 540 |
| ggttttagcc | ctcctttgc | ggtttcgcct | tttgttgggc | tggtctcact | tgcttgcaat | 600 |
| ctgtttgatg | gaatgcagga | gaggaggaat | gctgggaccg | ggggaggagc | cgcggctcgc | 660 |
| ggtgaggatc | tctttgtcgt | tgctgggttt | gggaatttcc | ggcgcgaaat | tatgtggatt | 720 |
| tctaggttta | tctgccgtct | ttcttcttgt | cttctctttt | ggctctgggg | tgagaagtta | 780 |
| gggtggttgg | gcggacatgg | tgcgttattt | cgccgtatcg | tttggtttgg | tgctttctca | 840 |
| tccttttaat | tccaacatgc | cttgtaaaaa | ttgcacaaga | tttgttttttt | catgcatgtc | 900 |
| tcagtgttgc | taatttgctt | ttccggttcg | gttggtagaa | ttcaatttct | tggcgcaata | 960 |
| tgcatcttct | tttgttgcaa | catgagggcg | aatgtgccag | ttccatatgg | gcgtcgcggt | 1020 |
| tttgaagtta | ctaccttgct | tgctcttcgt | attataggcg | tcattcacaa | tagtatgttt | 1080 |
| tcttggagat | gcagttgcac | ggggggcgtgt | ggagaagaag | catcgctggc | gggcagggac | 1140 |
| tgtagcgctg | cgggagatca | ggaagtacca | gaagtccact | gagccgctca | tcccctttgc | 1200 |
| gcccttcgta | cgtgtggtgg | gtgcatcttg | taccaattgt | tgtccactcc | atagaatggg | 1260 |
| tttgttctgc | agtctgtctg | atggaaagtt | attcttctga | gaaaaaatgc | aggtcaaaga | 1320 |
| gttaactgca | ttcataacag | actggaggat | agggcgctac | accccctgaag | ccctccttgc | 1380 |
| gctgcaagag | gtcagttatg | aaacatgtct | tgtgtatcag | ttaagatcat | cttctataga | 1440 |
| cataattgtt | atcatgaagt | ctttttctgt | taatcggtct | ggtactactt | aataatcagg | 1500 |
| atttcagatt | gctgccttc | ctagtggtgt | agtcaaaagg | gaatttaagt | gctgttaggt | 1560 |
| actgtttgtt | ttggtgtttt | gaaccctgcc | gcgatcggtt | gttgttattc | catgtttgtt | 1620 |

```
tctgtggcag cggacgttca cggtgagatg ggatacgggc gtgtgaaaca tagttacggt   1680
ccatcttcat ggcttatcca tttacgctgc tcgtccgctc acttgttatg tgcggcaacc   1740
aaacttttgt tactagtgta actggtagcg ttgcaaatct ttccatttgc gttaccactc   1800
cctatgggag ccaaacagca ccttagtgta gattccattt gtattacttg agctagcttc   1860
cttgctattg gtgcctcgat tgtactgtta tgatcgaagt gctgaaaact ttgtcgcctg   1920
catagcatga ttagagaact tgagtttaca tttattcaat accttaagac tgcatttcgt   1980
atagataaat tatttttcct aattgttctg gttaactgtt ttaggtttcc atattttgt    2040 atgtgtatca tttaaattat tgtgttgttt ttcctccctg tctacaggca gcagaattcc   2100
acttgataga actgtttgaa gtggcgaatc tgtgtgccat ccatgccaag cgcgtaacag   2160
tcagtaagtt atcactgaat gaactccttt tcctctgtac tattacgcct aatggagatg   2220
tgtgatgcat ttttggttac acgattcttt agtgattctg cttcagttgg atatgataaa   2280
tctagatgtt atttaaagtg gcaaattgct tacgagtgga atagtaatg ttcaaatagt    2340 gaaaagtgca attaaacttt taataggcca ttatatggtt tgattgtcaa caaatgcatc   2400
aagaaatagt aaatattata acagttatgg cttagagagt ggacaaaaaa tcggtaatgg   2460
tgagctttgt ataaacacta aaactggctg agaaatctga taactcaagg atctatagga   2520
aatgtattat cctaaatgtt ttccttcctg ctgcagtgca aaaggacata caacttgcaa   2580
ggcgtatcgg aggaaggcgt tggtcgtgat atccattctg attctgatta ccttgttcgg   2640
gtggaatttg tttagaggag ttagacatta gtcttgttga atgctgtgca tggttcctaa   2700
tctgtttcac agttagtggg ctcttctggg atgatctgtt aacacctgtg gagtatgtta   2760
tgtaggaaac acctgaactg aacaacccaa agttgttttg gttgctcttc aaccatttgt   2820
ttgcttcaga gatcgattct aaactgcatg ctaattagtc tatggttgaa caaaaattat   2880
caaatataaa tgaaagtgat atagtagcaa aatccaaaaa aaaaaggatc caaacaaggc   2940
ctaaaatcat ggttctttct ccttttgaac tgggtgcaag tatggacagg cacagaagaa   3000
aaccgcctag caaaccgttt gttttttttt cttcgttgta ccacacgaca ctgttcgttc   3060
ctagttgcgc cttttgttg tagaagtc                                       3088
```

<210> SEQ ID NO 16
<211> LENGTH: 471
<212> TYPE: DNA
<213> ORGANISM: Artificial Sequence
<220> FEATURE:
<223> OTHER INFORMATION: Sorghum bicolor - cDNA coding for CENH3

<400> SEQUENCE: 16

```
atggctcgaa ccaagcacca ggccgtgagg aagctgccgc agaagcccaa gaagaagctc    60
cagttcgagc gcgcaggtgg ggcgagtacg tcggcgaccc cggagaggag gaatgctggg   120
accgggggag gagccgcggc tcgcgttgca cgggggcgtg tggagaagaa gcatcgctgg   180
cgggcaggga ctgtagcgct gcgggagatc aggaagtacc agaagtccac tgagccgctc   240 atccccttg cgcccttcgt acgtgtggtc aaagagttaa ctgcattcat aacagactgg   300
aggatagggc gctacacccc tgaagccctc cttgcgctgc aagaggcagc agaattccac   360
ttgatagaac tgtttgaagt ggcgaatctg tgtgccatcc atgccaagcg cgtaacagtc   420
atgcaaaagg acatacaact tgcaaggcgt atcggaggaa ggcgttggtc g            471
```

<210> SEQ ID NO 17
<211> LENGTH: 157

<212> TYPE: PRT
<213> ORGANISM: Sorghum bicolor

<400> SEQUENCE: 17

```
Met Ala Arg Thr Lys His Gln Ala Val Arg Lys Leu Pro Gln Lys Pro
1               5                   10                  15

Lys Lys Lys Leu Gln Phe Glu Arg Ala Gly Gly Ala Ser Thr Ser Ala
            20                  25                  30

Thr Pro Glu Arg Arg Asn Ala Gly Thr Gly Gly Ala Ala Ala Arg
        35                  40                  45

Val Ala Arg Gly Arg Val Glu Lys Lys His Arg Trp Arg Ala Gly Thr
50                  55                  60

Val Ala Leu Arg Glu Ile Arg Lys Tyr Gln Lys Ser Thr Glu Pro Leu
65                  70                  75                  80

Ile Pro Phe Ala Pro Phe Val Arg Val Val Lys Glu Leu Thr Ala Phe
                85                  90                  95

Ile Thr Asp Trp Arg Ile Gly Arg Tyr Thr Pro Glu Ala Leu Leu Ala
            100                 105                 110

Leu Gln Glu Ala Ala Glu Phe His Leu Ile Glu Leu Phe Glu Val Ala
        115                 120                 125

Asn Leu Cys Ala Ile His Ala Lys Arg Val Thr Val Met Gln Lys Asp
    130                 135                 140

Ile Gln Leu Ala Arg Arg Ile Gly Gly Arg Arg Trp Ser
145                 150                 155
```

<210> SEQ ID NO 18
<211> LENGTH: 5834
<212> TYPE: DNA
<213> ORGANISM: Zea mays
<220> FEATURE:
<221> NAME/KEY: Intron
<222> LOCATION: (1820)..(1917)
<220> FEATURE:
<221> NAME/KEY: Intron
<222> LOCATION: (1944)..(2035)
<220> FEATURE:
<221> NAME/KEY: Intron
<222> LOCATION: (2085)..(2239)
<220> FEATURE:
<221> NAME/KEY: Intron
<222> LOCATION: (2356)..(2446)
<220> FEATURE:
<221> NAME/KEY: Intron
<222> LOCATION: (2525)..(4530)
<220> FEATURE:
<221> NAME/KEY: Intron
<222> LOCATION: (4607)..(5346)

<400> SEQUENCE: 18

| | | | | | |
|---|---|---|---|---|---|
| ttatgtagag | gcaattgcag | tagtgcctct | gttttagagt | gtaactacag | atttgtccct | 60 |
| atttttttag | agtttgcgtg | tttgtccctg | ttttttcaaa | tcaaactatt | gtataccct | 120 |
| actccattag | ttatacttaa | caatgttaag | tcttgataaa | aagacaaggg | ataattggat | 180 |
| tagtgaccct | gttttagagt | gtaattatag | ctttgcccga | tgttttagac | ttcacatgtt | 240 |
| tttatgacaa | ttcaaattgt | ttccataaca | tcttaaatta | ttttgacaac | atttagaatt | 300 |
| gttttgcaat | aatttaaatt | atttccaaaa | taaaatatt | ttgacaatta | ttttatcaac | 360 |
| aaattaaatt | atttttttta | caaaataatt | tgtcaaggta | cttttttaaa | attttgaaaa | 420 |
| taatcaaatt | attgtaaata | taatttgaat | tgttgcgaaa | ataatttgga | ttgtcataaa | 480 |
| aacacgtaag | tctaaaaatt | aggcgtaaaa | ctacaattat | actctaaaaa | ggtggtaatg | 540 |

-continued

```
gcgtagttgt tccttgtcta ttttatcaag acatagcacc gtgcagtaca actaatggag    600
tagtgacata caacaatttt gttttaaata atagggtaa atacgcaaag tctaaaaaac     660
agaggtaaat ctacaattac atgttaaaat agaggcatcg atacaattgt accttttata    720
tagcagcatg cgccctgttg ggatacaatt gtacctttca catgtcttct agatggttcc    780
caacccttTg gccaagatcg tacagataat attgcgagga gcccaaatca acggtgtcca    840
tatgttatgt tgatgtggat ggtttaccta ggcgcaaaag tgcgctggtt tcgtccgtac    900
aaatatactt taagtatggt tttgattttt ttctattttt catttttTaa ataaaacgag    960
acaatcaaat ctgatataaa aatcaaatga attataaata gagacggaaa gagtatatat   1020
atttgttttg ctattattta aagtattaaa agatagtgga cgaatgaacg tcctctatgt   1080 ttaaagaac gttttagagg acgttgtgtt gttgaaggaa atatgaaaaa aaaatcttct    1140
gcatatttag aagggaggag cgtttacaca ttactttcgg gacttcaacc caaatatgtc   1200
aaggtttgtg agtggctcag tgcgaaaaa aaatcctata taccagat gtaaacacta      1260 tcttttacag cctatcacat tcacatttag aggttcacaa agatagatca aaatttataa   1320
aataatcatt taatattttt ttatttttat ttatatggat aagcagctgg tgtatgtgag   1380
gagctgtaaa agatatttt tacatccgag atgtaaagat ttttttttaac tcaatgctgg   1440 ttaccggctg ggaggacgat gataaagaaa gcatctctca ctgcattccg ggcccactac   1500
tcaaacgttc ggcacgccag gttggcaggt agccgttaca tcgataggca ctcggccact   1560
cgcacgcaga caccacacca gtgtgctcag tgctcactgc tcaccataat aacgctgcac   1620
ctcttttcat ttcaccatct cctgccccct taaaaaaaag actcaccgtc gacacgccct   1680
cccgtcccga gagttctgaa tcgaaaccgt cggccacgag agcagtgcga ggcgcccacc   1740
gcgatggctc gaaccaagca ccaggccgtg aggaagacgg cggagaagcc caagaagaag   1800
ctccagttcg agcgctcagg taacccgggt cccgcgctcc ccccgcttc gcaagcagac    1860 gctgtcgctt ctctccgacc ctggtgctaa gcacgttcct tgttccgtct tttgcaggtg   1920
gtgcgagtac ctcggcgacg ccggtgagcg cgtgcgtgcg gggatcagtt ccctcctttt   1980 gcctttttt gttgggctgc tcttacttgc ttgcaagctg tttgatggaa tgcaggaaag    2040
ggctgctggg accgggggaa gagcggcgtc tggaggtgac tcaggtgagg acctatttgt   2100
cgttgctgga tgctgggttt cgcttgcaat ctaattttgt tgcaagatga gggcgaatgt   2160
gccagttcca tgtgggtgtc atggtctcgg agttactacc ttaattgctc accatagtat   2220
gttttcttaa aaaaaacagt taagaagacg aaaccacgcc accgctggcg gccagggact   2280
gtagcgctgc gggagatcag gaagtaccag aagtccactg aaccgctcat ccccttTgcg   2340
cctttcgtcc gtgtggtggg tgcaggcgtg tttgtcctct gcatagtatg gggttgttcc   2400
gcattctgtc taatggaaag ttattcttct gagaaaaaaa atgcaggtga gggagttaac   2460
caattTcgta acaaacggga aagtagagcg ctataccgca gaagccctcc ttgcgctgca   2520
agaggtcagt tatgaaaaat gtcttatctc tctgttaaga tcctcttcat atacatagtt   2580
gctattgcta tcgtgaagtc tttttttttct gttaattggt ctggtactac ttactagtca   2640
ggatttcata ttgcggtttt tcctagtggt gtgtagttaa aaagtagttt aattgctttt   2700
agttaaaagg ggtgttcagg gctaaagatc aactatgaga aaacagaaat tttcccaatt   2760
cgatacccga cagcattatg gcctgcgcta atggaggtgt tccgggcaa atactctagc    2820 ctacctggga agtaccttgg gttgcccctt catttcagga aagtaaaaag gaatgatctt   2880
caacctctaa tcgaaaaaat caacaacagg ctggccttgc tggaaaggca agatgttgtc   2940
```

```
caaggctggt atagaaactc ttgtaaaatc gatgctatcc gcacaaccaa tctaccatct  3000
aatggttttt ccacctcaaa aatggctgct gcaaacaatt gacaaaatac gaagaaactt  3060
cctgtggaga gggagcaatc cagaagtttg cagcgggggt cactgcctcg tcaactggcc  3120
cgtaacttgc ctcccaaaga acaagggagg tcttggaatt ctggaccttg atcgttttgc  3180 gaggggcta agactaagat ggctgtggct acgatggaag agcaaagata gggcgtggac  3240
tgccttgaag cttccttgtg acaaaactga tgaagatctc ttcaatgctt ccacaactgt  3300
cacggtaggc aatggaaaga tagctgaatt ctggaattct agttggatcc aaggccaagc  3360
ccctaagaac attgcgccaa cactgttcaa gaaggaaaag aggaagaaca tcacggtcgc  3420
caaagcgctc actaacaaca attggattcg tttatgctca ccatacacgg gtgaggggga  3480
gtttagagag gtcgtctctc tttggcaggc ataggtaac atgcaagagc ttaacgtttt  3540
ggaagacaac atctcttgga gatggacggc agatgggcag tacagtgcta gcagtgcata  3600
caaaatccag ttcgcatcca atttcactaa aatgaacctc tgccctattt ggaaggctaa  3660
agtggaaccg aaatgccgat tttttgcttg gacactactt cataagagaa ttctgactgc  3720
cgataacctt cataaaagag gttgcaactc agcctcagaa acaattcccc acttatgcaa  3780
ggattgcccc tttagtagag aggtgtggaa caaagttttg tctcgggcca actttccttt  3840
actgactggg tctcccagtg acacttcttt gtatgattgg tggacggaca tgtgcagcct  3900
ttgcagcaga caggcaagaa gaggtttcga cggtctgcta tttcactttt ggtggaactt  3960
atggctggaa agaaataaca gaatctttca aaggcagcgt agaagtgtag atcaagttgc  4020
tctggcagtc aaggattatg ctagtagctg aagtctagtt ggtttggact agtggttttg  4080
ttgcttttct ttttaatttc tttttagttc tttttatgtt gttttcgttt ccttaagttg  4140
cttggagtct gtattatcct ctttcttcta atatagatcg gagcgacaaa ccttttgccc  4200
cttcctttca aaaaaagtt aaagggaat ttaactgctt tcctagtggt gtagttaaaa  4260
tggatttcat attgcggcct ttcctagctt gcttgctatt gattggacta tagtgatcca  4320
aatgctgata actttgtcgc ttgtgtaggc atggttagag agcttagagt ttgcatttat  4380
tcaataccct gagactgcat ttcatataca taaattattc atgattattt cttttctcta  4440
tttgttctgg ttaattaaga gttttaggtt tccatatttt tgtacgtgca tcatttaaat  4500
tcttgtattg tttttcgttc ttgtctacag gcagcagaat tccacttgat agaactgttt  4560
gaaatggcga atctgtgtgc catccatgcc aagcgtgtca caatcagtaa gttatcactg  4620
agtgaactcc tttttctctg tagcattact cctaatgaat atgtgtgatg cattttggtt  4680
gcacgattct ttagtgattc tgcttcagat ggatatgata aatctagatg ttattttgaa  4740
gtggcgaatt gcttacgagc ggaaatagta atgttcaaat agcgcaaagt gcaactgttg  4800
acttttagta ggccatttat atggtttgat taccaacaaa tacgtcaatc atatgatttg  4860
attatcaaca aaggaatcag ctatatggtt tgattatcaa caaaggaatc agctaggttt  4920
gcttatcaac attcaacaaa ggcatcaagt aatactccat ccgtttcaat ttataattcg  4980
tttgactttt tttatctaag tttgatcggc tcgacttatt aaaaaaaatc ataattattg  5040 ttaattttg ttgtgatatt gtttagtata atatacttta aatgtgactt tgagtttttc  5100
attttttcgc aaaaaaaaat gaataggacg agccggtcaa acgtgacaca aaaaagtcaa  5160
acgaattata atttgggaca cacggagtag taaataatgt aacaacttag agagtgggac  5220
aaaaaaatct ctagtggtgc taaatttagt tcagctttgt ataaacacaa gcattgattg  5280
```

```
agaaatctga caactcaagg atctgtagga aatgtgttac cctaaatgtt ttccttactg    5340
atgcagtgca aaaggacata caacttgcaa ggcgtatcgg aggaaggcgt tgggcatgat    5400
atataatatc cattctgatt gcatcattct tgtgaatttg tttgtaggag ctagacatta    5460
gtgttgttga atgctgcatg gttcctaatc cttttcgcag tctaacatct gtggagttag    5520
tatgttacat ggcaacagct gaacatctgt ggactatatg caacagccg aagattgtgt     5580 ctgtgggata actggttgtt ttggttgctc ttcagtagtt tgtttgcttc aggtaaccat    5640
gctgcgaact atgatgtttt cattctcggt ttgcttcagc taaccgagat cgattcagtc    5700
tgcagtatgg actatggagt aaactgcatg ctgaaacccg aaccactgct gaaactgcat    5760
gctgaaaccc gaaccactgc tacggcagtt gccaggatag caggagggcc tttatgcaca    5820
gtggaattga gtag                                                     5834

<210> SEQ ID NO 19
<211> LENGTH: 471
<212> TYPE: DNA
<213> ORGANISM: Artificial Sequence
<220> FEATURE:
<223> OTHER INFORMATION: Zea mays - cDNA coding for CENH3

<400> SEQUENCE: 19
atggctcgaa ccaagcacca ggccgtgagg aagacggcgg agaagcccaa gaagaagctc      60
cagttcgagc gctcaggtgg tgcgagtacc tcggcgacgc cggaaagggc tgctgggacc     120
gggggaagag cggcgtctgg aggtgactca gttaagaaga cgaaaccacg ccaccgctgg     180
cggccaggga ctgtagcgct gcgggagatc aggaagtacc agaagtccac tgaaccgctc     240 atccccttt g cgcctttcgt ccgtgtggtg agggagttaa ccaatttcgt aacaaacggg     300
aaagtagagc gctataccgc agaagccctc cttgcgctgc aagaggcagc agaattccac     360
ttgatagaac tgtttgaaat ggcgaatctg tgtgccatcc atgccaagcg tgtcacaatc     420
atgcaaaagg acatacaact tgcaaggcgt atcggaggaa ggcgttgggc a              471

<210> SEQ ID NO 20
<211> LENGTH: 157
<212> TYPE: PRT
<213> ORGANISM: Zea mays

<400> SEQUENCE: 20

Met Ala Arg Thr Lys His Gln Ala Val Arg Lys Thr Ala Glu Lys Pro
1               5                  10                  15

Lys Lys Lys Leu Gln Phe Glu Arg Ser Gly Gly Ala Ser Thr Ser Ala
            20                  25                  30

Thr Pro Glu Arg Ala Ala Gly Thr Gly Gly Arg Ala Ala Ser Gly Gly
        35                  40                  45

Asp Ser Val Lys Lys Thr Lys Pro Arg His Arg Trp Arg Pro Gly Thr
    50                  55                  60

Val Ala Leu Arg Glu Ile Arg Lys Tyr Gln Lys Ser Thr Glu Pro Leu
65                  70                  75                  80

Ile Pro Phe Ala Pro Phe Val Arg Val Val Arg Glu Leu Thr Asn Phe
                85                  90                  95

Val Thr Asn Gly Lys Val Glu Arg Tyr Thr Ala Glu Ala Leu Leu Ala
            100                 105                 110

Leu Gln Glu Ala Ala Glu Phe His Leu Ile Glu Leu Phe Glu Met Ala
        115                 120                 125
```

```
Asn Leu Cys Ala Ile His Ala Lys Arg Val Thr Ile Met Gln Lys Asp
    130                 135                 140

Ile Gln Leu Ala Arg Arg Ile Gly Gly Arg Arg Trp Ala
145                 150                 155

<210> SEQ ID NO 21
<211> LENGTH: 8441
<212> TYPE: DNA
<213> ORGANISM: Beta vulgaris
<220> FEATURE:
<221> NAME/KEY: Intron
<222> LOCATION: (99)..(203)
<220> FEATURE:
<221> NAME/KEY: Intron
<222> LOCATION: (245)..(331)
<220> FEATURE:
<221> NAME/KEY: Intron
<222> LOCATION: (344)..(488)
<220> FEATURE:
<221> NAME/KEY: Intron
<222> LOCATION: (591)..(3263)
<220> FEATURE:
<221> NAME/KEY: Intron
<222> LOCATION: (3339)..(4377)
<220> FEATURE:
<221> NAME/KEY: Intron
<222> LOCATION: (4458)..(8130)

<400> SEQUENCE: 21
ctactctttc tctctctctc tctctccatt tctgtttgaa atcatgagag ttaaacacac      60
tgctgccagg aaatcaacca ccaacggtcc tcgttcaagt tagtttcctc tctcttcttc     120
ttttttgttc gcattctctc aatctatatt tcaaatttga aaaaaattgt gatgctcata     180
aaccctaaaa ttttcttgta cagaggctca gaaatctccg cgcagtttgc aatcaccaca     240
atcggttctc tctttgtact tttgatttgt ttttccttca tttgttcgat gaatggctct     300
taattgtctt ttatttactt gaaaattgca gccttctagt agttcaaagc gcaaatcact     360
cagaaacact gatgcaactc ctcaaagtaa cttttttctttt aatattaggt ttaattttac     420
tgctgtttgc caaattctgt tgaaattgta aaatatttttt tttcttaaat ttgacggttt     480
cagagaagaa ggcttaccgc cgtaagccgg gcactgtggc actctgggaa atacgcaaat     540
ttcagaagtc attcaagccc ttgattcctg ctgcgccttt cattcgaaca gtatgtattt     600
tttttgtttg tacttaataa atgaattttg gactggtgtt tgtgtggctg catagaaata     660
tatttccata caactgaaat tgtcctagga ggtatcgatg aatgtttgct acaaaataaa     720
taaatataag tgattatatc ttgttaaaaa gccattataa ttgcaactta tatgtatgtt     780
gtaatgaggt caactagcta ttttgtgcaa agtcacccac actttaacat aattttgtgc     840
tctcgtaacc ttaaaaaaat ataagtaaag ggttgatttg gtctaattag agctgatgaa     900
acccaattag attgaaacat aaggtgaaat caggtggtga tcagcttcaa ttagatctaa     960
taagtgcagt ttagtttagc ttcggtgaaa tgaacacacc cttaaagata gaaaatcgac    1020
actatatatg gtccttttta gatatgatag ttcgatattc tgttttgggg tgtgttgaat    1080
gattaaatgg agtggtgaat agctgatggg aactagagaa gatgctcagt agacagttat    1140
tgtggagact atattactga ttacccctgt ttctgagtgg ttaggacaat gtgacaattg    1200
attttgggta ttatttgtag atgttttttct tttttgttaaa agtgccaaga taggtgtgca    1260
gttgctgatt ctcagtttgc taagaattag ctgtgtctgt atttcgtacc tcagttgatt    1320
ctaagtgaac atttctttga attgatgctt tgttcttgca tcatgcaact tggtgaagct    1380
```

```
ttcttgtagt tgctccagtg gcaatctagt ctggtatgtt tagaactctt gtgatggtat    1440
gagttcatca agatattggt gatccaatta gcctaaccaa tgttttttac cccctattgt    1500
cactgactta tactccctta tctataaaaa taattgtgac attgatccat ctcctcacaa    1560
tcattaatat tatatgtact gaccatcttt acactctcaa cactgaatct aagtagggga    1620
attttgggaa attcaatgat gaactagtac acccttcttc ccaataatat tgttgacctt    1680
tttattttga tttgtcccat attgtcctct ttggtaattt aatgtatatt cacccaattt    1740
tcttttcaat acccactata ccaacatata attggttaat tcattttat taattatatt     1800 tcctaagagc ttgttgtgta aacgtggatg aatttgtagg catggatgaa gtattgttat    1860
aatgaggtga caacattact taatttcgaa ctgagggaca gagggatatg atgataaaac    1920
aacttttgct tgcttcttaa actcagaaga tagggtttac accaagtggc atgtaaaagt    1980
cactagatga ttatctatta caagggcttg tacaatctga agtacgatag gatttgaagt    2040
taacaacatt catcgaaagc tcataacttg tccttatatc aatataagtt gctggcatgt    2100
gaaattgcgt tgcaagcatc catgagctag ctcaactatt aactattaaa ctttatattt    2160
ttgcttgatc tagtatgagt cctactattt agtttctcca tctaccttaa tatgtcgcat    2220
acaccaacta atcattatcg ctagaatcaa taaacaaagc tttctttcct taggtgtatt    2280
agtacctagc tcctgtaata ccaagagcac ccaaattggg aagaaaaagt agaattggct    2340
catatctcta atcctacatt gatcattgaa aaggacctta aggttctcat actgaaacat    2400
catctttttg agcaggatat ctacgtagac gacaagaaag actactttgg ttgcccgtgc    2460
atttgagtgc atcagacaac ttctttacca ctgtctaacg gcttgctttg gccatattgt    2520
ggtcttctat gccaaaatta atgatatttc ttggcaccgc gctaatgata ttactgaatg    2580
cggatatcgt acgattagaa tttattcaaa gtaggtagca attactagtt ttgagcattg    2640
agtttcaata attagtaaat taagtgctaa acttgtacat tttggctaca tgtatttgaa    2700
ttagaattgg tacgaggaaa tatagcaaca ttacgggcaa tgttcactca agtagaagcc    2760
attacatcaa atagtactag ttgaagtatt agttctcata atactaatca ttgtcattaa    2820
tggaatattg gaacgtaaat gccttttaagg tgctgtagtt ttagtagaaa ttctactatt    2880
ctagtatgat aatgcaattt attgaaactg tttgtaagat agcttggatc ccacatcagt    2940
cttgatgcta aataaatgga tgtccataat cttctaatct ttaatttgtg tctcttacca    3000
aacgagaaaa aataggagaa atccaatttg catgacctca ataaggaaat gttgttaatg    3060
tgtgatgctt gttctctcatt tatagtctag agagagttat catgtccaag attgcagtct    3120
tggtactgag aaagtttgat tgttggttgg ctgcttcttg agcctctttt ttttagagta    3180
agacacttcc tagatataat tttctttatt tttttgtaaa ttccatatat actactacat    3240
taacaggttt aagtttatat taggtgagag agattactca ccagtttgct ccttatgttg    3300
gtcgttggca agctgaagct ctgatggccc ttcaagaggt gcagaccaac tcttttagcc    3360 ttttttttc tggcatgtca agtgtggcta ttagattttc tgtgtgattc tcactcccat     3420
atatctatat atgtacatat taaagcacat tgatacctat cttgtcagat gtggtctttt    3480
caattctttt ctaagttgag attcttctct tggtcgtaga tatgctcctg ccgaaatata    3540
ctgctgtctt gttatccatc atgacttggt tatgcttgta tctgggcatt atcttggcat    3600
gcttaaaaac aagtattgaa cgagcctcct attgataaat tttactatta atattggatg    3660
gcttctcaaa ttctaatggc agtgagatac tgttaagttg ggagaaatag attaagaaac    3720
agaaagatgt ttaccatgag agcaattgaa atagaaaata gagtaacttt ttgcaaagat    3780
```

```
tttggtcctt tagattgttg aatactacct gataatgaag catttttctaa atttatgtgc    3840 tttctatcta tcagatactg gaatacaatc aaattcctat cacgtactga gcattgtgat    3900
cagattcttg cttgcttcct atcacatact ggaatccttt tgattgttga atacaaagat    3960
aatgaagcat tctctaactt tatgtgctgt aactactat aatgattctt gcttgcctcc    4020
tatcacgtac tcaaatcctt tgtttgattt gtctcttata agaggaactt cctgtctttc    4080
tttgtcatga cttagtattt atagaggtgc caacttatgg ccttgacaac tgaagctttt    4140
atgcaaactc cggattttgt tgatggaagt acaagtaaca ctttagcatg tggattcagg    4200
tctaacggtt aagactttt aatgaatgtt ttaactgtag tagtttattg atataaaaaa    4260
agtggtctct caaactttt atgagatcat atcgaagtaa tcaaatttat gattcaggtg    4320
cttctgctat tattcttggt taagcatgtg ctatttttga cagtctgtca attgtaggct    4380
gcagagaatt ttattgtccg tttgtttgaa gatggtatgc tttgtgcaat tcatgccaaa    4440
cgagttacac tcagtgagta tctgattcc ttcggtggtg ctgctattat gcattatata    4500
cactttgcct caatatcgtt atataaggag tccttgtttt catatttgtt tgatgcatat    4560
gttatatcct gttagtggc tgctgcagtt gtgaacttac ggcctgtttg attagtggtc    4620
ataaatgatg gtaatactaa tataatttag tataaatttg taaaaaaaat gctaatatca    4680
atatttatgg taatgaaatt ttatcataaa acatgagttc tcttttataa gttttcatta    4740
ctatccaata ccaccttccc aagtggtaat gaacggtaat gaaatttag gaagaaaatg    4800 gatatttggg gattagatag cattaccatg ggtaatgaca tgagattttc tttacaactt    4860
tatactacga tgcattatca ttaccaccat ttatgaccca taaccaaaaa aaccataatg    4920
tgttaggttc atttttcatt tttctaataa tttgcttcat gaattttttc tggagatatc    4980
ttatctagat atttcttgcc aacatgtttc acctgataat tgatcgattt aatagttcag    5040
aactttccaa aaactatgct gctcggtgtt ggctgtcatc catcagttta agaaaactat    5100
tgacatgatt taagcctcgt cctgtactac taggaagggt aaactattgt tgcttccaaa    5160
aatgtctttt aagggcgtgt tcagcaacaa tagttgtagt agtagctttt agctgttagt    5220
tgtgctcgta gctgttagtg gttagtgtgt aactgttagc tgttcaagta gcggtataag    5280
atattgatgt tcggtaaaag aagctgtcaa aatagctgtt tacaaagaat taataaaaaa    5340
ctcaaacaaa gctttaatat ataatttatg caccactaaa gctaccccaa aagctacaaa    5400
ttgtagcttt ttacaaacac tactaaaaca ctacttgtaa cactaaaagc tacttatact    5460
actattttgc caaacattat tattttttct taattagtgt tttgacctag tcaagacact    5520
aaaagctact tgaaaagctt ttgccgaaca cgcccttagt agacaagagg ggggagggggg    5580 tcatcaagaa aatatgatta tactctcaac aaaaaaaaaa tgtaacttaa aaaaaataaa    5640
aataaataat tgactacttc aattaagaaa agaatagaat aaaaacatta cagtggatgt    5700
ctcatccaca tccctaattt aatggcacaa tagataatt gttttaaatt ttagaaatta    5760
caacacaaga tgtaaattac tcttatcttc ctcttcgtaa tcttttttact cttcctttac    5820 ctcttccttt acctctacat aaaatagaga attagagatt gattaagata attataagat    5880
tttagaaaca ttggttaaga aattcttcaa caaacataat caagtaactc cattatttta    5940
gtttagtgac ttgctatta tcaccctaat ttcaccatct accgccctcc ttggacaata    6000
ttgccccttc cactttcttc actcttcctt cctcacgcat cttatcatct ccttccacta    6060
tcacctttaa aaaagtgtgt caggcacaac aaaaacgctt ttatcaaccc acgcgaggcg    6120
```

```
aagtacgtca ggcgcaacaa ggcgcgcacc taattctgtc ttttgccaag gctgatggtg      6180
cacttagttt taaaaagcgc agcaaagatg tgcctaggcg caaggcggtg aaaaaattgc      6240
atccgtcagc agcggagtag aggctcacaa caataggtgc gaagaggcgt gcacgtacaa      6300
aagaagcaaa aataagaaac tcaaatatga gacccagtgt ttaacatgta aattcgatac      6360
ccagtgttta acatgtaaat tcgattaaaa gcccttaatt aattgcatga aattaattca      6420
ttttaaccta tactaaaagc cctaatatta gaaaatccta gtttgcaggt tgaggaattt      6480
ggaaaattga tgattgttgg atttgaaaaa attgttgccg gcgatgaatg tgaggtggtt      6540
tatggcacta gagaggttgg cgttcgttgc cgatgaagct ttccaaggtc attctctcct      6600
tgtcttcttc ctatgcctag ctctcttccc tctccttaat cttctcttct tttctattct      6660
ctctctttat cactacatta tgtttatttc tcgttcttcc cctatgtctt tcacttggac      6720
acttcggggg tatcttcatc ttttatctgc aatttgaagt ttgagaagct tccagagtcg      6780
agtgttaaac ttttgcttct tttttttttaa tcttttgccc ttttttctta gtggcccttg      6840
actagtgatg cacatgtgac caattactaa atgagctttt attttgtctc tcttcttttt      6900
caagcaattt tttttaagta aatcatctaa aacaaagtac tatccatttt agttgtgtaa      6960
atggtgctat tttaaaaccg cacaaaaatt aaaaacataa aaataaaggt gtgcttcgca      7020
tacaagatgt atgcgccttc gtcttgcccc ttttgagact aagactacca taagaactta      7080
gtcacttgag aatggaatgg gtgcaagatg gacgacgata attctaaaga cctctagaag      7140
gatagtgtat agtaactaat acgaaccgaa atataagttt aactaaaatt ttaaagtcta      7200
tatttccata tggtatatgc tggaatacac gaaatgtcca gaatttgtag tggaccacga      7260
tccacacgtc ttttcaggat tctaggtgta ttccaacgaa aaatataaga aaaccatatt      7320
ctactatctg gttgttgtca tccttttcctt gccggcgtga cttctcatcc ttttattttt      7380
gtccggtgct ggtgacacac tttcctatga tagtgtggtg caaagtaagg tgatgatatg      7440
gtgttttgta gaggtgtggt gattttttgtg gtggtgggtg gaagagggggt ggttgcatat      7500 agaaaggggt aagagtcaat gagggggtgga aggggacaag gggtatattg gtaaatgcat      7560
gtaacattag ggtggtgttg agtaattttt gggaagttaa tataaactac ccccttttgg      7620
tacaagagag aatacccgaa ctactgctct gatattttttg ttcacgttat ttgatgtaat      7680
tacgcaatta atttgtttttc tataagcttc cgcacacaat tgtgcatata aggctagtct      7740
aatatgagac accaacataa ctgactttct tttgcaacga aggtaccttg tcagatttag      7800
aacatagcat caggatttta tttgttgtat ctgtcatcct tgtttattgc tttaattatg      7860
ctttgtatga tgcattttac cacttcgtat gaaaaaaagt gaaatttcat ttagtggtca      7920
tttacatatt acgagttgtg gacatgtttg aacatttgat tttggaaatt ttaagcctca      7980
tattatggag atttattgga cacaaatata gccataattc tccatcaact tgtttctaga      8040
agtgttgctc ttcctgatgt acttgaattc taattaggtt ttatcagaca ttatattata      8100
atgatatgat ttacaatttg ttgtagtgaa aaaggattttg gagctcgcgc gaaggattgg      8160
gggcagagag aggggatggt aactaaacaa cacagatgac tcatttattt aagggccaac      8220
aattgaattc gctgttgatt tcatctgtat atactgctct aggcttctat tccaatgtaa      8280
tttataaatc caaggttagt agcatgttaa gctttgtatt cagtataatg agacttatat      8340
tttgcagttg agattttagt tgtttgatgt gacttgtaaa ttgtaacttg taagtgacgt      8400
cttgaggatt atcgggacaa tatactattt ttttttttcaa a                        8441
```

<210> SEQ ID NO 22
<211> LENGTH: 462
<212> TYPE: DNA
<213> ORGANISM: Artificial Sequence
<220> FEATURE:
<223> OTHER INFORMATION: Sorghum bicolor - cDNA coding for CENH3

<400> SEQUENCE: 22

```
atgagagtta aacacactgc tgccaggaaa tcaaccacca atggtcctcg ttcaaaggct        60
cagaaatctc cgcgcagttt gcaatcacca caatcgcctt ctagtagttc aaagcgcaaa       120
tcacgcagaa acactgatgc aactcctcaa aagaagaagg cttaccgccg taagccgggc       180
actgtggcac tctgggaaat acgcaaattt cagaagtcat tcaagccctt gattcctgct       240
gcgcctttca ttcgaacagt gagagagatt actcaccagt ttgctcctta tgttggtcgt       300
tggcaagctg aagctctgat ggcccttcaa gaggctgcag agaattttat tgtccgtttg       360
tttgaagatg gtatgctttg tgcaattcat gccaaacgag ttacactcat gaaaaaggat       420
ttggagctcg cgcgaaggat tgggggcaga gagagggat gg                          462
```

<210> SEQ ID NO 23
<211> LENGTH: 154
<212> TYPE: PRT
<213> ORGANISM: Beta vulgaris

<400> SEQUENCE: 23

```
Met Arg Val Lys His Thr Ala Ala Arg Lys Ser Thr Thr Asn Gly Pro
1               5                   10                  15

Arg Ser Lys Ala Gln Lys Ser Pro Arg Ser Leu Gln Ser Pro Gln Ser
            20                  25                  30

Pro Ser Ser Ser Lys Arg Lys Ser Arg Arg Asn Thr Asp Ala Thr
        35                  40                  45

Pro Gln Lys Lys Lys Ala Tyr Arg Arg Lys Pro Gly Thr Val Ala Leu
    50                  55                  60

Trp Glu Ile Arg Lys Phe Gln Lys Ser Phe Lys Pro Leu Ile Pro Ala
65                  70                  75                  80

Ala Pro Phe Ile Arg Thr Val Arg Glu Ile Thr His Gln Phe Ala Pro
                85                  90                  95

Tyr Val Gly Arg Trp Gln Ala Glu Ala Leu Met Ala Leu Gln Glu Ala
            100                 105                 110

Ala Glu Asn Phe Ile Val Arg Leu Phe Glu Asp Gly Met Leu Cys Ala
        115                 120                 125

Ile His Ala Lys Arg Val Thr Leu Met Lys Lys Asp Leu Glu Leu Ala
    130                 135                 140

Arg Arg Ile Gly Gly Arg Glu Arg Gly Trp
145                 150
```

<210> SEQ ID NO 24
<211> LENGTH: 4597
<212> TYPE: DNA
<213> ORGANISM: Artificial Sequence
<220> FEATURE:
<223> OTHER INFORMATION: Z. mays CENH3-Mu-mutation
<220> FEATURE:
<221> NAME/KEY: misc_recomb
<222> LOCATION: (676)..(685)
<223> OTHER INFORMATION: transposon insertion

<400> SEQUENCE: 24

```
agagacggaa agagtatata tatttgtttt gctattattt aaagtattaa aagatagtgg    60
acgaatgaac gtcctctatg tttaaaagaa cgttttagag gacgttgtgt tgttgaagga   120
aatatgaaaa aaaaatcttc tgcatattta gaagggagga gcgtttacac attactttcg   180
ggacttcaac ccaaatatgt caaggtttgt gagtggctca gtgcggaaaa aaaatcctat   240
atataccaga tgtaaacact atcttttaca gcctatcaca ttcacattta gaggttcaca   300
aagatagatc aaaatttata aaataatcat ttaatatttt ttttatttta tttatatgga   360
taagcagctg gtgtatgtga ggagctgtaa aagatatttt ttacatccga gatgtaaaga   420
ttttttttaa ctcaatgctg gttaccggct gggaggacga tgataaagaa agcatctctc   480
actgcattcc gggcccacta ctcaaacgtt cggcacgcca ggttggcagg tagccgttac   540
atcgataggc actcggccac tcgcacgcag acaccacacc agtgtgctca gtgctcactg   600
ctcaccataa taacgctgca cctctttca tttcaccatc tcctgccccc ttaaaaaaaa   660
gactcaccgt cgacacgccc tcccgtcccg agagttctga atcgaaaccg tcggccacga   720
gagcagtgcg aggcgcccac cgcgatggct cgaaccaagc accaggccgt gaggaagacg   780
gcggagaagc ccaagaagaa gctccagttc gagcgctcag gtaacccggg tcccgcgctc   840
cccccccgctt cgcaagcaga cgctgtcgct tctctccgac cctggtgcta agcacgttcc   900
ttgttccgtc ttttgcaggt ggtgcgagta cctcggcgac gccggtgagc gcgtgcgtgc   960
ggggatcagt tccctccttt tgccttttt tgttgggctg ctcttacttg cttgcaagct  1020
gtttgatgga atgcaggaaa gggctgctgg gaccggggga agagcggcgt ctggaggtga  1080
ctcaggtgag gacctatttg tcgttgctgg atgctgggtt tcgcttgcaa tctaattttg  1140
ttgcaagatg agggcgaatg tgccagttcc atgtgggtgt catggtctcg gagttactac  1200
cttaattgct caccatagta tgttttctta aaaaaaacag ttaagaagac gaaaccacgc  1260
caccgctggc ggccagggac tgtagcgctg cgggagatca ggaagtacca gaagtccact  1320
gaaccgctca tcccctttgc gcctttcgtc cgtgtggtgg gtgcaggcgt gtttgtcctc  1380
tgcatagtat ggggttgttc cgcattctgt ctaatgaaaa gttattcttc tgagaaaaaa  1440
aatgcaggtg agggagttaa ccaatttcgt aacaaacggg aaagtagagc gctataccgc  1500
agaagccctc cttgcgctgc aagaggtcag ttatgaaaaa tgtcttatct ctctgttaag  1560
atcctcttca tatacatagt tgctattgct atcgtgaagt cttttttttc tgttaattgg  1620
tctggtacta cttactagtc aggatttcat attgcggttt ttcctagtgg tgtgtagtta  1680
aaaagtagtt taattgcttt tagttaaaag gggtgttcag ggctaaagat caactatgag  1740
aaaacagaaa ttttcccaat tcgatacccg acagcattat ggcctgcgct aatggaggtg  1800
tttccgggca aatactctag cctacctggg aagtaccttg ggttgcccct tcatttcagg  1860
aaagtaaaaa ggaatgatct tcaacctcta atcgaaaaaa tcaacaacag gctggccttg  1920
ctggaaaggc aagatgttgt ccaaggctgg tatagaaact cttgtaaaat cgatgctatc  1980
cgcacaacca atctaccatc taatggtttt tccacctcaa aaatggctgc tgcaaacaat  2040
tgacaaaata cgaagaaact tcctgtggag agggagcaat ccagaagttt gcagcggggg  2100
tcactgcctc gtcaactggc ccgtaacttg cctcccaaag aacaagggag gtcttggaat  2160
tctggacctt gatcgttttg cgaggggct aagactaaga tggctgtggc tacgatggaa  2220
gagcaaagat agggcgtgga ctgccttgaa gcttccttgt gacaaaactg atgaagatct  2280
```

```
cttcaatgct tccacaactg tcacggtagg caatggaaag atagctgaat tctggaattc    2340
tagttggatc caaggccaag cccctaagaa cattgcgcca acactgttca agaaggaaaa    2400
gaggaagaac atcacggtcg ccaaagcgct cactaacaac aattggattc gtttatgctc    2460
accatacacg ggtgaggggg agtttagaga ggtcgtctct ctttggcagg ccataggtaa    2520
catgcaagag cttaacggtt tggaagacaa catctcttgg agatggacgg cagatgggca    2580
gtacagtgct agcagtgcat acaaaatcca gttcgcatcc aatttcacta aaatgaacct    2640 ctgcccctatt tggaaggcta agtggaaccc gaaatgccga ttttttgctt ggacactact    2700
tcataagaga attctgactg ccgataacct tcataaaaga ggttgcaact cagcctcaga    2760
aacaattccc cacttatgca aggattgccc ctttagtaga gaggtgtgga acaaagtttt    2820
gtctcgggcc aactttcctt tactgactgg gtctcccagt gacacttctt tgtatgattg    2880
gtggacggac atgtgcagcc tttgcagcag acaggcaaga agaggtttcg acggtctgct    2940
atttcacttt tggtggaact tatggctgga agaaataac agaatctttc aaaggcagcg    3000
tagaagtgta gatcaagttg ctctggcagt caaggattat gctagtagct gaagtctagt    3060
tggtttggac tagtggtttt gttgcttttc ttttaattt cttttagtt ctttttatgt    3120 tgttttcgtt tccttaagtt gcttggagtc tgtattatcc tctttcttct aatatagatc    3180
ggagcgacaa accttttgcc ccttcctttc aaaaaaaagt taaaaggaa tttaactgct    3240 ttcctagtgg tgtagttaaa atggatttca tattgcggcc tttcctagct tgcttgctat    3300
tgattggact atagtgatcc aaatgctgat aactttgtcg cttgtgtagg catggttaga    3360
gagcttagag tttgcattta ttcaatacct tgagactgca tttcatatac ataaattatt    3420
catgattatt tcttttctct atttgttctg gttaattaag agtttttaggt ttccatattt    3480 ttgtacgtgc atcattttaaa ttcttgtatt gtttttcgtt cttgtctaca ggcagcagaa    3540
ttccacttga tagaactgtt tgaaatggcg aatctgtgtg ccatccatgc caagcgtgtc    3600
acaatcagta agttatcact gagtgaactc cttttctct gtagcattac tcctaatgaa    3660
tatgtgtgat gcattttggt tgcacgattc tttagtgatt ctgcttcaga tggatatgat    3720
aaatctagat gttattttga agtggcgaat tgcttacgag cggaaatagt aatgttcaaa    3780
tagcgcaaag tgcaactgtt gacttttagt aggccatttta tatggtttga ttaccaacaa    3840
atacgtcaat catatgattt gattatcaac aaaggaatca gctatatggt ttgattatca    3900
acaaaggaat cagctaggtt tgcttatcaa cattcaacaa aggcatcaag taatactcca    3960
tccgtttcaa tttataattc gtttgacttt ttttatctaa gtttgatcgg ctcgacttat    4020
taaaaaaaat cataattatt gttaattttt gttgtgatat tgtttagtat aatatacttt    4080
aaatgtgact ttgagttttt catttttttcg caaaaaaaaa tgaataggac gagccggtca    4140
aacgtgacac aaaaaagtca aacgaattat aatttgggac acacggagta gtaaataatg    4200
taacaactta gagagtggga caaaaaaatc tctagtggtg ctaaatttag ttcagctttg    4260
tataaacaca agcattgatt gagaaatctg acaactcaag gatctgtagg aaatgtgtta    4320
ccctaaatgt tttccttact gatgcagtgc aaaaggacat acaacttgca aggcgtatcg    4380
gaggaaggcg ttgggcatga tatataatat ccattctgat tgcatcattc ttgtgaattt    4440
gtttgtagga gctagacatt agtgttgttg aatgctgcat ggttcctaat cctttctgca    4500
gtctaacatc tgtggagtta gtatgttaca tggcaacagc tgaacatctg tggactatat    4560
ggcaacagcc gaagattgtg tctgtgggat aactggt                              4597
```

GENERATION OF HAPLOID PLANTS

CROSS-REFERENCE TO RELATED APPLICATIONS

This application is a divisional of U.S. application Ser. No. 15/539,065, filed Jun. 22, 2017, which is a U.S. national phase application under 35 U.S.C. § 371 of International Patent Application No. PCT/EP2015/081158, filed Dec. 23, 2015, which published as International Application No. WO 2016/102665 A2, on Jun. 30, 2016 and claims priority to European Patent Application No. 14004389.4, filed Dec. 23, 2014, the disclosures of all of which are hereby incorporated by reference in their entirety.

SEQUENCE LISTING

The instant application contains a Sequence Listing which has been submitted in ASCII format via EFS-Web and is hereby incorporated by reference in its entirety. Said ASCII copy, created on Jun. 5, 2017, is named 245761000116_Sequence_Listing_ST2.txt, and is 50,114 bytes in size.

FIELD OF THE INVENTION

The present invention relates to non-transgenic and transgenic plants, preferably crop plants, having biological activity of a haploid inducer and comprising a polynucleotide which comprises a nucleotide sequence encoding a centromeric histone H3 (CENH3) protein, wherein the polynucleotide comprises at least one mutation causing an alteration of the amino acid sequence of the CENH3 protein and said alteration confers the biological activity of a haploid inducer. Further, the present invention provides methods of generating the plants of the present invention and haploid and double haploid plants obtainable by crossing the plants of the present invention with wildtype plants as well as methods of facilitating cytoplasm exchange.

BACKGROUND OF THE INVENTION

The generation and use of haploids is one of the most powerful biotechnological means to improve cultivated plants. The advantage of haploids for breeders is that homozygosity can be achieved already in the first generation after dihaploidization, creating doubled haploid plants, without the need of several backcrossing generations required to obtain a high degree of homozygosity. Further, the value of haploids in plant research and breeding lies in the fact that the founder cells of doubled haploids are products of meiosis, so that resultant populations constitute pools of diverse recombinant and at the same time genetically fixed individuals. The generation of doubled haploids thus provides not only perfectly useful genetic variability to select from with regard to crop improvement, but is also a valuable means to produce mapping populations, recombinant inbreds as well as instantly homozygous mutants and transgenic lines.

Haploids can be obtained by in vitro or in vivo approaches. However, many species and genotypes are recalcitrant to these processes. Alternatively, substantial changes of the centromere-specific histone H3 variant (CENH3, also called centromeric histone H3 or CENP-A), by swapping its N-terminal regions and fusing it to GFP ("GFP-tailswap" CENH3), creates haploid inducer lines in the model plant *Arabidopsis thaliana* (Ravi and Chan, Nature, 464 (2010), 615-618; Comai, L, "Genome elimination: translating basic research into a future tool for plant breeding.", PLoS biology, 12.6 (2014)). CENH3 proteins are variants of H3 histone proteins that are members of the kinetochore complex of active centromeres. With these "GFP-tailswap" haploid inducer lines, haploidization occurred in the progeny when a haploid inducer plant was crossed with a wildtype plant. Interestingly, the haploid inducer line was stable upon selfing, suggesting that a competition between modified and wild type centromere in the developing hybrid embryo results in centromere inactivation of the inducer parent and consequently in uniparental chromosome elimination. As a result, the chromosomes containing the altered CENH3 protein are lost during early embryo development producing haploid progeny containing only the chromosomes of the wildtype parent.

Thus, haploid plants can be obtained by crossing "GFP-tailswap" transgenic plants as haploid inducer to wildtype plants. However, as described above, this technique requires substantial changes of the CENH3 protein and the plants comprise a heterologous transgene, which is economically problematic because of increasing public reluctance toward genetically engineered crops.

It is therefore an object of the present invention to overcome the aforementioned problems and in particular to provide alternative haploid inducer plants which do not comprise substantial modifications of their CENH3 protein and/or which are not genetically engineered.

BRIEF DESCRIPTION OF THE DRAWINGS

FIG. 1 shows an alignment of the amino acid sequences of *Arabidopsis thaliana* (first row), *Beta vulgaris* (second row), *Brassica napus* (third row), *Zea mays* (fourth row), *Sorghum bicolor* (fifth row) as well as a diagram showing the level of conservation over these five plant species.

DETAILED DESCRIPTION OF THE INVENTION

This problem is solved by the subject matter of the independent claims, in particular by a plant having biological activity of a haploid inducer and comprising a polynucleotide which comprises a nucleotide sequence encoding a centromeric histone H3 (CENH3) protein wherein the polynucleotide comprises at least one mutation causing an alteration of the amino acid sequence of the CENH3 protein and said alteration confers the biological activity of a haploid inducer. In the context of the present invention the term 'alteration' means any modification of the amino acid sequence of the protein CENH3 (including multiple modifications) which are caused by at least one mutation in the polynucleotide which comprises a nucleotide sequence encoding a centromeric histone H3 (CENH3) protein. The polynucleotide can be a genomic DNA of the CENH3 gene, the cDNA of CENH3, or 5'- or 3'-untranslated regions of the CENH3 gene or a mixture thereof that comprises for instances a part of the genomic DNA and a part of the cDNA. An alteration can be a substitution of one or more amino acids, an insertion of one or more amino acids or a deletion of one or more amino acids. Mutations at DNA level which are able to alter the amino acid sequence of the protein CENH3 can be point mutations leading to an amino acid substitution or a stop codon, insertions or deletion which shift the reading frame of the CENH3 gene, or mutations in the splicing sites.

In a preferred embodiment, the at least one mutation causes the alteration of the amino acid sequence of the protein CENH3 which confers the biological activity of a haploid inducer in at least one segment of the amino acid sequence of the CENH3 protein. The sequence segment is selected from the group consisting of N-terminal tail domain, CATD domain, αN-helix, α1-helix, loop1, α2-helix, loop2, α3-helix, and C-terminal domain. The N-terminal tail domain of the CENH3 protein corresponds to amino acid sequence from position 1 to position 82 as set forth in SEQ ID NO: 11 derived from *Arabidopsis thaliana* and/or the N-terminal tail domain of the CENH3 protein is encoded by a nucleotide sequence corresponding to nucleotides from position 1 to position 246 as set forth in SEQ ID NO: 10 derived from *Arabidopsis thaliana*. The CATD domain of the CENH3 protein corresponds to amino acid sequence from position 113 to position 155 as set forth in SEQ ID NO: 11 derived from *Arabidopsis thaliana* and/or the CATD domain of the CENH3 protein is encoded by a nucleotide sequence corresponding to nucleotides from position 337 to position 465 as set forth in SEQ ID NO: 10 derived from *Arabidopsis thaliana*. The αN-helix of the CENH3 protein corresponds to amino acid sequence from position 83 to position 97 as set forth in SEQ ID NO: 11 derived from *Arabidopsis thaliana* and/or the αN-helix of the CENH3 protein is encoded by a nucleotide sequence corresponding to nucleotides from position 247 to position 291 as set forth in SEQ ID NO: 10 derived from *Arabidopsis thaliana*. The α1-helix of the CENH3 protein corresponds to amino acid sequence from position 103 to position 113 as set forth in SEQ ID NO: 11 derived from *Arabidopsis thaliana* and/or the α1-helix of the CENH3 protein is encoded by a nucleotide sequence corresponding to nucleotides from position 307 to position 339 as set forth in SEQ ID NO: 10 derived from *Arabidopsis thaliana*. The loop1 of the CENH3 protein corresponds to amino acid sequence from position 114 to position 126 as set forth in SEQ ID NO: 11 derived from *Arabidopsis thaliana* and/or the loop1 of the CENH3 protein is encoded by a nucleotide sequence corresponding to nucleotides from position 340 to position 378 as set forth in SEQ ID NO: 10 derived from *Arabidopsis thaliana*. The α2-helix of the CENH3 protein corresponds to amino acid sequence from position 127 to position 155 as set forth in SEQ ID NO: 11 derived from *Arabidopsis thaliana* and/or the α2-helix of the CENH3 protein is encoded by a nucleotide sequence corresponding to nucleotides from position 379 to position 465 as set forth in SEQ ID NO: 10 derived from *Arabidopsis thaliana*. The loop2 of the CENH3 protein corresponds to amino acid sequence from position 156 to position 162 as set forth in SEQ ID NO: 11 derived from *Arabidopsis thaliana* and/or the loop2 of the CENH3 protein is encoded by a nucleotide sequence corresponding to nucleotides from position 466 to position 486 as set forth in SEQ ID NO: 10 derived from *Arabidopsis thaliana*. The α3-helix of the CENH3 protein corresponds to amino acid sequence from position 163 to position 172 as set forth in SEQ ID NO: 11 derived from *Arabidopsis thaliana* and/or the α3-helix of the CENH3 protein is encoded by a nucleotide sequence corresponding to nucleotides from position 487 to position 516 as set forth in SEQ ID NO: 10 derived from *Arabidopsis thaliana*. The C-terminal domain of the CENH3 protein corresponds to amino acid sequence from position 173 to position 178 as set forth in SEQ ID NO: 11 derived from *Arabidopsis thaliana* and/or the C-terminal domain of the CENH3 protein is encoded by a nucleotide sequence corresponding to nucleotides from position 517 to position 534 as set forth in SEQ ID NO: 10 derived from *Arabidopsis thaliana*. The *A. thaliana* sequences serve only as references and do not limit the invention to the particular *A. thaliana* sequences. Due to the high level of conservation ones skilled in the art is able to find the nucleotide sequence and amino acid sequence corresponding to the *A. thaliana* sequences in any other plant material or plant species.

CENH3 proteins are variants of H3 histone proteins that are members of the kinetochore complex of active centromeres, i.e. the protein structure on chromosomes where spindle fibres attach during cell division. Basically, CENH3 proteins are characterized by a variable N-terminal tail domain, which does not form a rigid secondary structure, and a conserved histone fold domain consisting of three α-helical regions, termed α1 to α3, which are connected by two loop sections. The N-terminal tail domain is primarily subject to post translational modification by enzymes. Such modifications include methylation, citrullination, phosphorylation, SUMOylation, ubiquitination, and ADP-ribosylation and affect the function of regulation of the CENH3 gene. Within the histone fold domain the highly conserved CATD domain (CENP-A targeting domain) is located, which is formed by parts of the α1-helix, the complete α2-helix and the connecting loop1. The conserved CATD domain is required for CENH3 loading by chaperones and thus vital for its kinetochore localization and centromere function. N-terminal tail domain and histone fold domain are linked by the αN-helix.

The present inventors surprisingly found that a plant possessing the capability to produce haploid progeny, i.e. a haploid inducer, can be obtained not only by alteration of the amino acid sequence of the conserved CENH3 protein, but also by alteration of the amino acid sequence of any other domain and structural regions of the CENH3 gene and CENH3 protein. In addition, the capability to produce haploid progeny can be further enhanced by combination of two or more alterations of the amino acid sequence of the CENH3 protein in different domains, segments or structural regions of the CENH3 protein. Hence, the efficiency of haploid production can be increased significantly. Advantageously, this can be achieved by transgenic as well as non-transgenic methods. Non-transgenic methods are preferred because of enormous costs for deregulation of genetically modified organisms (GMO) as well as increasing public rejection of genetically modified organisms (GMO) or plants generated by means of GMO, in particular crops for human consumption, and extensive market authorisation processes including rigorous safety assessments of such GMOs.

The present invention provides a plant comprising and expressing a CENH3 protein, wherein the plant comprises a polynucleotide and the polynucleotide comprising the nucleotide sequence of the gene encoding the CENH3 protein comprises at least one mutation causing the alteration of the amino acid sequence of the CENH3 protein in at least one segment of the amino acid sequence of the CENH3 protein, wherein the segment is selected from the group consisting of the N-terminal tail domain, most preferred the N-terminal tail domain having the consensus sequence of SEQ ID NO: 1 and SEQ ID NO: 2, the αN-helix, most preferred the αN-helix having the consensus sequence of SEQ ID NO: 3, the α1-helix, most preferred the α1-helix having the consensus sequence of SEQ ID NO: 4, the loop1, most preferred the loop1 having the consensus sequence of SEQ ID NO: 5, the α2-helix, most preferred the α2-helix having the consensus sequence of SEQ ID NO: 6, the loop2, most preferred the loop2 having the consensus sequence of SEQ ID NO: 7, the 3-helix, most preferred the α3-helix having the consensus sequence of SEQ ID NO: 8 and the C-terminal domain, most preferred the C-terminal domain having the consensus sequence of SEQ ID NO: 9. The alteration of the amino acid sequence of the CENH3 protein can confer the biological activity of a haploid inducer to the plant. In a preferred embodiment the present invention relates to a plant comprising a polynucleotide which comprises a nucleotide sequence encoding a centromeric histone H3 (CENH3) protein, wherein the polynucleotide comprises at least one mutation and wherein the at least one mutation causes an alteration of the amino acid sequence of the CENH3 protein in at least one segment of the amino acid sequence of the CENH3 protein. The segment can be a) the N-terminal tail domain which is encoded by a nucleotide sequence corresponds to nucleotides from position 1 to position 246 as set forth in SEQ ID NO: 10 derived from *Arabidopsis thaliana*, corresponds to amino acid sequence from positions 1 to position 82 as set forth in SEQ ID NO: 11 derived from *Arabidopsis thaliana*, or is encoded by a nucleotide sequence corresponds to nucleotides from position 1 to position 177 as set forth in SEQ ID NO: 22 derived from *Beta vulgaris*, corresponds to amino acid sequence from positions 1 to position 59 as set forth in SEQ ID NO: 23 derived from *Beta vulgaris*, or is encoded by a nucleotide sequence corresponds to nucleotides from position 1 to position 252 as set forth in SEQ ID NO: 13 derived from *Brassica napus*, corresponds to amino acid sequence from positions 1 to position 84 as set forth in SEQ ID NO: 14 derived from *Brassica napus*, or is encoded by a nucleotide sequence corresponds to nucleotides from position 1 to position 186 as set forth in SEQ ID NO: 19 derived from *Zea mays*, corresponds to amino acid sequence from positions 1 to position 62 as set forth in SEQ ID NO: 20 derived from *Zea mays*, or is encoded by a nucleotide sequence corresponds to nucleotides from position 1 to position 186 as set forth in SEQ ID NO: 16 derived from *Sorghum bicolor*, corresponds to amino acid sequence from positions 1 to position 62 as set forth in SEQ ID NO: 17 derived from *Sorghum bicolor*, or having the consensus sequence of SEQ ID NO: 1 and SEQ ID NO: 2, b) the αN-helix which is encoded by a nucleotide sequence corresponds to nucleotides from position 247 to position 291 as set forth in SEQ ID NO: 10 derived from *Arabidopsis thaliana*, corresponds to amino acid sequence from positions 83 to position 97 as set forth in SEQ ID NO: 11 derived from *Arabidopsis thaliana*, or is encoded by a nucleotide sequence corresponds to nucleotides from position 178 to position 222 as set forth in SEQ ID NO: 22 derived from *Beta vulgaris*, corresponds to amino acid sequence from positions 60 to position 74 as set forth in SEQ ID NO: 23 derived from *Beta vulgaris*, or is encoded by a nucleotide sequence corresponds to nucleotides from position 253 to position 297 as set forth in SEQ ID NO: 13 derived from *Brassica napus*, corresponds to amino acid sequence from positions 85 to position 99 as set forth in SEQ ID NO: 14 derived from *Brassica napus*, or is encoded by a nucleotide sequence corresponds to nucleotides from position 187 to position 231 as set forth in SEQ ID NO: 19 derived from *Zea mays*, corresponds to amino acid sequence from positions 63 to position 77 as set forth in SEQ ID NO: 20 derived from *Zea mays*, or is encoded by a nucleotide sequence corresponds to nucleotides from position 187 to position 231 as set forth in SEQ ID NO: 16 derived from *Sorghum bicolor*, corresponds to amino acid sequence from positions 63 to position 77 as set forth in SEQ ID NO: 17 derived from *Sorghum bicolor*, or having the consensus sequence of SEQ ID NO: 3, c) the α1-helix which is encoded by a nucleotide sequence corresponds to nucleotides from position 307 to position 339 as set forth in SEQ ID NO: 10 derived from *Arabidopsis thaliana*, corresponds to amino acid sequence from positions 103 to position 113 as set forth in SEQ ID NO: 11 derived from *Arabidopsis thaliana*, or is encoded by a nucleotide sequence corresponds to nucleotides from position 238 to position 270 as set forth in SEQ ID NO: 22 derived from *Beta vulgaris*, corresponds to amino acid sequence from positions 80 to position 90 as set forth in SEQ ID NO: 23 derived from *Beta vulgaris*, or is encoded by a nucleotide sequence corresponds to nucleotides from position 313 to position 345 as set forth in SEQ ID NO: 13 derived from *Brassica napus*, corresponds to amino acid sequence from positions 105 to position 115 as set forth in SEQ ID NO: 14 derived from *Brassica napus*, or is encoded by a nucleotide sequence corresponds to nucleotides from position 247 to position 279 as set forth in SEQ ID NO: 19 derived from *Zea mays*, corresponds to amino acid sequence from positions 83 to position 93 as set forth in SEQ ID NO: 20 derived from *Zea mays*, or is encoded by a nucleotide sequence corresponds to nucleotides from position 247 to position 279 as set forth in SEQ ID NO: 16 derived from *Sorghum bicolor*, corresponds to amino acid sequence from positions 83 to position 93 as set forth in SEQ ID NO: 17 derived from *Sorghum bicolor*, or having the consensus sequence of SEQ ID NO: 4, d) the loop1 which is encoded by a nucleotide sequence corresponds to nucleotides from position 340 to position 378 as set forth in SEQ ID NO: 10 derived from *Arabidopsis thaliana*, corresponds to amino acid sequence from positions 114 to position 126 as set forth in SEQ ID NO: 11 derived from *Arabidopsis thaliana*, or is encoded by a nucleotide sequence corresponds to nucleotides from position 271 to position 306 as set forth in SEQ ID NO: 22 derived from *Beta vulgaris*, corresponds to amino acid sequence from positions 91 to position 102 as set forth in SEQ ID NO: 23 derived from *Beta vulgaris*, or is encoded by a nucleotide sequence corresponds to nucleotides from position 346 to position 384 as set forth in SEQ ID NO: 13 derived from *Brassica napus*, corresponds to amino acid sequence from positions 116 to position 128 as set forth in SEQ ID NO: 14 derived from *Brassica napus*, or is encoded by a nucleotide sequence corresponds to nucleotides from position 280 to position 318 as set forth in SEQ ID NO: 19 derived from *Zea mays*, corresponds to amino acid sequence from positions 94 to position 106 as set forth in SEQ ID NO: 20 derived from *Zea mays*, or is encoded by a nucleotide sequence corresponds to nucleotides from position 280 to position 318 as set forth in SEQ ID NO: 16 derived from *Sorghum bicolor*, corresponds to amino acid sequence from positions 94 to position 106 as set forth in SEQ ID NO: 17 derived from *Sorghum bicolor*, or having the consensus sequence of SEQ ID NO: 5, e) the α2-helix which is encoded by a nucleotide sequence corresponds to nucleotides from position 379 to position 465 as set forth in SEQ ID NO: 10 derived from *Arabidopsis thaliana*, corresponds to amino acid sequence from positions 127 to position 155 as set forth in SEQ ID NO: 11 derived from *Arabidopsis thaliana*, or is encoded by a nucleotide sequence corresponds to nucleotides from position 307 to position 393 as set forth in SEQ ID NO: 22 derived from *Beta vulgaris*, corresponds to amino acid sequence from positions 103 to position 131 as set forth in SEQ ID NO: 23 derived from *Beta vulgaris*, or is encoded by a nucleotide sequence corresponds to nucleotides from position 385 to position 471 as set forth in SEQ ID NO: 13 derived from *Brassica napus*, corresponds to amino acid sequence from positions 129 to position 157 as set forth in SEQ ID NO: 14 derived from Brassica napus, or is encoded by a nucleotide sequence corresponds to nucleotides from position 319 to position 405 as set forth in SEQ ID NO: 19 derived from *Zea mays*, corresponds to amino acid sequence from positions 107 to position 135 as set forth in SEQ ID NO: 20 derived from *Zea mays*, or is encoded by a nucleotide sequence corresponds to nucleotides from position 319 to position 405 as set forth in SEQ ID NO: 16 derived from *Sorghum bicolor*, corresponds to amino acid sequence from positions 107 to position 135 as set forth in SEQ ID NO: 17 derived from *Sorghum bicolor*, or having the consensus sequence of SEQ ID NO: 6, f) the loop2 which is encoded by a nucleotide sequence corresponds to nucleotides from position 466 to position 486 as set forth in SEQ ID NO: 10 derived from *Arabidopsis thaliana*, corresponds to amino acid sequence from positions 156 to position 162 as set forth in SEQ ID NO: 11 derived from *Arabidopsis thaliana*, or is encoded by a nucleotide sequence corresponds to nucleotides from position 394 to position 414 as set forth in SEQ ID NO: 22 derived from *Beta vulgaris*, corresponds to amino acid sequence from positions 132 to position 138 as set forth in SEQ ID NO: 23 derived from *Beta vulgaris*, or is encoded by a nucleotide sequence corresponds to nucleotides from position 472 to position 492 as set forth in SEQ ID NO: 13 derived from *Brassica napus*, corresponds to amino acid sequence from positions 158 to position 164 as set forth in SEQ ID NO: 14 derived from *Brassica napus*, or is encoded by a nucleotide sequence corresponds to nucleotides from position 406 to position 426 as set forth in SEQ ID NO: 19 derived from *Zea mays*, corresponds to amino acid sequence from positions 136 to position 142 as set forth in SEQ ID NO: 20 derived from *Zea mays*, or is encoded by a nucleotide sequence corresponds to nucleotides from position 406 to position 426 as set forth in SEQ ID NO: 16 derived from *Sorghum bicolor*, corresponds to amino acid sequence from positions 136 to position 142 as set forth in SEQ ID NO: 17 derived from *Sorghum bicolor*, or having the consensus sequence of SEQ ID NO: 7, g) the α3-helix which is encoded by a nucleotide sequence corresponds to nucleotides from position 487 to position 516 as set forth in SEQ ID NO: 10 derived from *Arabidopsis thaliana*, corresponds to amino acid sequence from positions 163 to position 172 as set forth in SEQ ID NO: 11 derived from *Arabidopsis thaliana*, or is encoded by a nucleotide sequence corresponds to nucleotides from position 415 to position 444 as set forth in SEQ ID NO: 22 derived from *Beta vulgaris*, corresponds to amino acid sequence from positions 139 to position 148 as set forth in SEQ ID NO: 23 derived from *Beta vulgaris*, or is encoded by a nucleotide sequence corresponds to nucleotides from position 493 to position 522 as set forth in SEQ ID NO: 13 derived from *Brassica napus*, corresponds to amino acid sequence from positions 165 to position 174 as set forth in SEQ ID NO: 14 derived from *Brassica napus*, or is encoded by a nucleotide sequence corresponds to nucleotides from position 427 to position 456 as set forth in SEQ ID NO: 19 derived from *Zea mays*, corresponds to amino acid sequence from positions 143 to position 152 as set forth in SEQ ID NO: 20 derived from *Zea mays*, or is encoded by a nucleotide sequence corresponds to nucleotides from position 427 to position 456 as set forth in SEQ ID NO: 16 derived from *Sorghum bicolor*, corresponds to amino acid sequence from positions 143 to position 152 as set forth in SEQ ID NO: 17 derived from *Sorghum bicolor*, or having the consensus sequence of SEQ ID NO: 8, or h) the C-terminal domain which is encoded by a nucleotide sequence corresponds to nucleotides from position 517 to position 534 as set forth in SEQ ID NO: 10 derived from *Arabidopsis thaliana*, corresponds to amino acid sequence from positions 173 to position 178 as set forth in SEQ ID NO: 11 derived from *Arabidopsis thaliana*, or is encoded by a nucleotide sequence corresponds to nucleotides from position 445 to position 462 as set forth in SEQ ID NO: 22 derived from *Beta vulgaris*, corresponds to amino acid sequence from positions 149 to position 154 as set forth in SEQ ID NO: 23 derived from *Beta vulgaris*, or is encoded by a nucleotide sequence corresponds to nucleotides from position 523 to position 540 as set forth in SEQ ID NO: 13 derived from *Brassica napus*, corresponds to amino acid sequence from positions 175 to position 180 as set forth in SEQ ID NO: 14 derived from *Brassica napus*, or is encoded by a nucleotide sequence corresponds to nucleotides from position 457 to position 471 as set forth in SEQ ID NO: 19 derived from *Zea mays*, corresponds to amino acid sequence from positions 153 to position 157 as set forth in SEQ ID NO: 20 derived from *Zea mays*, or is encoded by a nucleotide sequence corresponds to nucleotides from position 457 to position 471 as set forth in SEQ ID NO: 16 derived from *Sorghum bicolor*, corresponds to amino acid sequence from positions 153 to position 157 as set forth in SEQ ID NO: 17 derived from *Sorghum bicolor*, or having the consensus sequence of SEQ ID NO: 9. Part of α1-helix, the complete loop and complete α2-helix are positioned within the CATD domain of the CENH3 protein as defined above. The non-mutated N-terminal tail domain of the CENH3 protein is partly conserved among plant species (see FIG. 1). In the present invention, any amino acid position given with respect to these two conserved parts of the N-terminal tail domain (part A and part B) or the below described consensus sequence is referring to the following numbering system. Conserved part A and part B of the N-terminal tail domain can be separated by one or more amino acids. The specific number varies from plant species to plant species. For that in the consensus sequence a "*" has been introduced as place holder. Preferably, the non-mutated N-terminal tail domain exhibits the amino acid sequence as given in Table 1.

TABLE 1

Specified amino acids in the N-terminal tail domain of the CENH3 protein

| Conserved part - position within the N-terminal | Amino acid(s) |
|---|---|
| A/1 | M |
| A/2 | A |
| A/3 | R |
| A/4 | T, V, I or A |
| A/5 | K or R |
| A/6 | H, T, Q or K |
| A/7 | X |
| A/8 | X |
| A/9 | V, A, P, G, N, P, R, S or H |
| A/10 | T, R, S, L, K, H, N, A or P |
| A/11 | R, K, A, N or T |
| A/12 | S, A, T, L, K, R, D, N or E |
| A/13 | Q, T, R, A, P, S, G, N, V, K or R |
| A/14 | P, T, D, E, Q, S, N, G, A, K or R |
| A/15 | R, N, H, V, G, K, S, A, T, E or P |
| B/1 | R, D, K, V, G, P, S, Q, T or A |
| B/2 | G, A, S, K, R, V, T, P or Q |
| B/3 | S, T, K, V, R, Q, A, E, G, P or D |
| B/4 | Q, P, N, T, E, K, G, S, R, A or D |
| B/5 | K, Q, P, G, N, T, H or R |
| B/6 | X |
| B/7 | K, R, Q or H |
| B/8 | K, Q or R |
| B/9 | S, A, T, K, P or R |
| B/10 | Y, F, H, T, K, R, F or Q |

TABLE 1-continued

Specified amino acids in the N-terminal tail domain of the CENH3 protein

| Conserved part - position within the N-terminal | Amino acid(s) |
|---|---|
| B/11 | R |
| B/12 | Y, R, W, F, L, N or S |
| B/13 | R or K |
| B/14 | P, A or S |

More preferably, the N terminal tail domain has the consensus sequences of SEQ ID NO: 1 (part A, before *) and SEQ ID NO: 2 (part B, beyond *), which is

```
MARTK HXXAR RSRKR * QSQTQ XKKKH RYRP.
    5    10    15     5    10    14
```

As indicated above, the N-terminal tail domain comprises unspecified [marked as X] and specified amino acids [marked as one letter code]. Instead of an unspecified amino acid the "X" can also be a gap of at least one amino acid.

The non-mutated αN-helix of the CENH3 protein is highly conserved among plant species and is 15 amino acids long starting with position 1 and ending with position 15. In the present invention, any amino acid position given with respect to the αN-helix or the below described consensus sequence of SEQ ID NO: 3 is referring to this numbering system. Preferably, the non-mutated αN-helix exhibits the amino acid sequence as given in Table 2.

TABLE 2

Specified amino acids in the αN-helix of the CENH3 protein

| Position within the αN-helix | Amino acid(s) |
|---|---|
| 1 | G |
| 2 | T |
| 3 | V |
| 4 | A |
| 5 | L |
| 6 | K, W or R |
| 7 | E or Q |
| 8 | I |
| 9 | R |
| 10 | X |
| 11 | F, Y or L |
| 12 | Q or R |
| 13 | K |
| 14 | Q, S or T |
| 15 | T, F, W, V, C or A |

More preferably, the αN-helix has the consensus sequence of SEQ ID NO: 3, which is

```
GTVAL REIRX FQKTT.
    5    10    15
```

As indicated above, the αN-helix comprises unspecified [marked as X] and specified amino acids [marked as one letter code].

The non-mutated α1-helix of the CENH3 protein is highly conserved among plant species and is 11 amino acids long starting with position 1 and ending with position 11. In the present invention, any amino acid position given with respect to the α1-helix or the below described consensus sequence of SEQ ID NO: 4 is referring to this numbering system. Preferably, the non-mutated α1-helix exhibits the amino acid sequence as given in Table 3.

TABLE 3

Specified amino acids in the α1-helix of the CENH3 protein

| Position within the α1-helix | Amino acid(s) |
|---|---|
| 1 | A, F, R or S |
| 2 | A, M or S |
| 3 | S, P, T, A or C |
| 4 | F |
| 5 | I, V, M, L, S or A |
| 6 | R |
| 7 | E, T, V, L, C, Q or A |
| 8 | V or I |
| 9 | R or K |
| 10 | S, E, M, T, E, Q, G or D |
| 11 | I, V, L or T |

More preferably, the α1-helix has the consensus sequence of SEQ ID NO: 4, which is

```
AAPFI RLVRE I.
    5    10
```

As indicated above, the α1-helix comprises specified amino acids [marked as one letter code].

The non-mutated loop1 of the CENH3 protein is highly conserved among plant species and is 13 amino acids long starting with position 1 and ending with position 13. In the present invention, any amino acid position given with respect to the loop1 or the below described consensus sequence of SEQ ID NO: 5 is referring to this numbering system. Preferably, the non-mutated loop1 exhibits the amino acid sequence as given in Table 4.

TABLE 4

Specified amino acids in the loop1 of the CENH3 protein

| Position within the loop1 | Amino acid(s) |
|---|---|
| 1 | T, S or A |
| 2 | H, Q, N, A, Y, F, G, D or E |
| 3 | M, Q, I, F, Y, A, E, N, R, L, H or G |
| 4 | L, F, V, I or Y |
| 5 | A, T, S, C or M |
| 6 | P, N, D, R, A, T, F, R, H, S or K |
| 7 | X |
| 8 | Q, Y, D, K, R, E, G, S, P, H, N or A |
| 9 | I, V or P |
| 10 | N, G, T, E, or S |
| 11 | R or P |
| 12 | W or Y |
| 13 | T, Q or S |

More preferably, the loop1 has the consensus sequence of SEQ ID NO: 5, which is

```
TNFLA PXEVT RWT.
    5    10   13
```

As indicated above, the loop1 comprises unspecified [marked as X] and specified amino acids [marked as one letter code].

The non-mutated α2-helix of the CENH3 protein is highly conserved among plant species and is 29 amino acids long starting with position 1 and ending with position 29. In the present invention, any amino acid position given with respect to the α2-helix or the below described consensus sequence of SEQ ID NO: 6 is referring to this numbering system. Preferably, the non-mutated α2-helix exhibits the amino acid sequence as given in Table 5.

TABLE 5

Specified amino acids in the α2-helix of the CENH3 protein

| Position within the α2-helix | Amino acid(s) |
| --- | --- |
| 1 | A, P, V or L |
| 2 | E, D, Q, H or L |
| 3 | A |
| 4 | L or V |
| 5 | V, L, M, I, R, Y or T |
| 6 | S or A |
| 7 | I or L |
| 8 | Q |
| 9 | E |
| 10 | A or S |
| 11 | A or T |
| 12 | E |
| 13 | D, N, F, I or Y |
| 14 | Y, F or H |
| 15 | L, I or V |
| 16 | V or I |
| 17 | G, R, E, H, N, T, E, D or Q |
| 18 | L, M or I |
| 19 | F, M or L |
| 20 | S, E, D or G |
| 21 | D, M, V, N, E, A, R or K |
| 22 | S, G, A or T |
| 23 | M, W, N or H |
| 24 | L or H |
| 25 | C or L |
| 26 | A or T |
| 27 | L or I |
| 28 | H |
| 29 | A or S |

More preferably, the α2-helix has the consensus sequence of SEQ ID NO: 6, which is

```
AEALL ALQEA AEDFL VHLFE DAMLC AIHA.
    5    10   15    20    25   29
```

As indicated above, the α2-helix comprises specified amino acids [marked as one letter code].

The non-mutated loop2 of the CENH3 protein is highly conserved among plant species and is 7 amino acids long starting with position 1 and ending with position 7. In the present invention, any amino acid position given with respect to the loop2 or the below described consensus sequence of SEQ ID NO: 7 is referring to this numbering system. Preferably, the non-mutated loop2 exhibits the amino acid sequence as given in Table 6.

TABLE 6

Specified amino acids in the loop2 of the CENH3 protein

| Position within the loop2 | Amino acid(s) |
| --- | --- |
| 1 | R, K or H |
| 2 | R |
| 3 | V or I |
| 4 | T |
| 5 | L, I or V |
| 6 | M or L |
| 7 | R, K, Q, L or T |

More preferably, the loop2 has the consensus sequence of SEQ ID NO: 7, which is

```
KRVTL MK.
  5   7
```

As indicated above, the loop2 comprises specified amino acids [marked as one letter code]. The non-mutated α3-helix of the CENH3 protein is highly conserved among plant species and is 10 amino acids long starting with position 1 and ending with position 10. In the present invention, any amino acid position given with respect to the α3-helix or the below described consensus sequence of SEQ ID NO: 8 is referring to this numbering system. Preferably, the non-mutated α3-helix exhibits the amino acid sequence as given in Table 7.

TABLE 7

Specified amino acids in the α3-helix of the CENH3 protein

| Position within the α3-helix | Amino acid(s) |
| --- | --- |
| 1 | K or R |
| 2 | D |
| 3 | F, L, I, M or W |
| 4 | E, Q or R |
| 5 | L |
| 6 | A or T |
| 7 | R |
| 8 | R |
| 9 | L or I |
| 10 | G, R or T |

More preferably, the α3-helix has the consensus sequence of SEQ ID NO: 8, which is

```
KDFEL ARRLG.
   5     10
```

As indicated above, the α3-helix comprises specified amino acids [marked as one letter code]. The non-mutated C-terminal domain of the CENH3 protein varies in length. Under consideration of numerous plant species (see below) we identified length of up to 7 amino acids. In the present invention, any amino acid position given with respect to the C-terminal domain or the below described consensus sequence of SEQ ID NO: 9 is referring to this numbering system. Preferably, the non-mutated C-terminal domain exhibits the amino acid sequence as given in Table 8.

TABLE 8

Specified amino acids in the C-terminal domain of the CENH3 protein

| Position within the C-terminal domain | Amino acid(s) |
| --- | --- |
| 1 | G, K, A, S or T |
| 2 | K, R, I or A |
| 3 | G, E or A |
| 4 | R, Q or V |
| 5 | P, G, I, Q, L, S or H |
| 6 | W, L, F or V |
| 7 | X |

More preferably, the C-terminal domain has the consensus sequence of SEQ ID NO: 9, which is

```
GKGRP W.
    5 6
```

As indicated above, the C-terminal domain comprises specified amino acids [marked as one letter code].

According to one preferred embodiment of the present invention, a mutation causing an alteration of any of the unspecified or the specified amino acid as defined in Table 1 or in SEQ ID NO: 1 or 2, or in Table 2 or in SEQ ID NO: 3, or in Table 3 or in SEQ ID NO: 4, or in Table 4 or in SEQ ID NO: 5, or in Table 5 or in SEQ ID NO: 6, or in Table 6 or in SEQ ID NO: 7, in Table 7 or in SEQ ID NO: 8, or in Table 8 or in SEQ ID NO: 9, preferably a substitution or deletion of the amino acid(s), can produce the desired plant possessing the capability to produce haploid progeny.

An unspecified amino acid as given in Table 1 or in SEQ ID NO: 1 or 2, or in Table 2 or in SEQ ID NO: 3, or in Table 3 or in SEQ ID NO: 4, or in Table 4 or in SEQ ID NO: 5, or in Table 5 or in SEQ ID NO: 6, or in Table 6 or in SEQ ID NO: 7, in Table 7 or in SEQ ID NO: 8, or in Table 8 or in SEQ ID NO: 9 is an amino acid which although being specified in a group of particular plant species, in a particular plant genus or in a particular plant species is not conserved in a greater range of plant species. Thus, an unspecified amino acid of SEQ ID NO: 1, 2, 3, 4, 5, 6, 7, 8 or 9 or as given in Table 1, Table 2, Table 3, Table 4, Table 5, Table 6, Table 7 or Table 8 is in a group of particular plant species, in a particular plant genus or in a particular plant species a well-defined, specific amino acid, which, however, is possibly not found at the same place in another plant species. Thus, an amino acid substitution of an unspecified amino acid of SEQ ID NO: 1 or as indicated in Table 1 means that in a plant, namely in a specific plant species, the specific but not conserved amino acid is substituted by another amino acid than naturally occurring at that place in this group of particular plant species, in this particular plant genus or in this particular plant species in the endogenously coded native CENH3 protein of said plant species. Furthermore, an unspecified amino acid as well as a specified amino acid can be essential with respect to processes of protein folding or protein stability. The alteration of such amino acid can lead to a mutant CENH3 having impaired stability or an incorrect folding.

Specified amino acids given in Table 1, Table 2, Table 3, Table 4, Table 5, Table 6, Table 7 or Table 8 and in particular specified amino acids of SEQ ID NO: 1, 2, 3, 4, 5, 6, 7, 8 or 9 are those which occur in a broad range of plant species, preferably such as listed below, and which are thus well conserved.

In a preferred embodiment, the consensus sequence of SEQ ID NO: 1, 2, 3, 4, 5, 6, 7, 8 and 9 has been compiled from the sequences of the protein segments derived from species selected from the group consisting of *Hordeum vulgare, Hordeum bulbusom, Sorghum bicolor, Saccharum officinarium, Zea mays, Setaria italica, Oryza minuta, Oriza satia, Oryza australiensis, Oryza alta, Triticum aestivum, Secale cereale, Malus domestica, Brachypodium distachyon, Hordeum marinum, Aegilops tauschii, Daucus glochidiatus, Beta vulgaris, Daucus pusillus, Daucus muricatus, Daucus carota, Eucalyptus grandis, Nicotiana sylvestris, Nicotiana tomentosiformis, Nicotiana tabacum, Solanum lycopersicum, Solanum tuberosum, Coffea canephora, Vitis vinfera, Erythrante guttata, Genlisea aurea, Cucumis sativus Morus notabilis, Arabidopsis arenosa, Arabidopsis lyrata, Arabidopsis thaliana, Crucihimalaya himalaica, Crucihimalaya wallichii, Cardamine flexuosa, Lepidium virginicum, Capsella bursa pastoris, Olmarabidopsis pumila, Arabis hirsute, Brassica napus, Brassica oeleracia, Brassica rapa, Raphanus sativus, Brassica juncea, Brassica nigra, Eruca vesicaria subsp, satia, Citrus sinensis, Jatropha curcasPopulus trichocarpa, Medicago truncatula, Cicer yamashitae, Cicer bijugum, Cicer arietinum, Cicer reticulatum, Cicer judaicum, Cajanus cajanfolius, Cajanus scarabaeoides, Phaseolus vulgaris, Glycine max, Astragalus sinicus Lotus japonicas, Torenia fournieri, Allium cepa, Allium fistulosum, Allium sativum*, and *Allium tuberosum*.

In a particularly preferred embodiment, the at least one mutation causes a substitution of a specified amino acid as defined in Table 1, Table 2, Table 3, Table 4, Table 5, Table 6, Table 7 or Table 8. Thus, the plant according to the present invention comprises at least one substitution of the specified amino acids as defined in Table 1, Table 2, Table 3, Table 4, Table 5, Table 6, Table 7 or Table 8, i.e. those amino acids which are conserved and named in Table 1, Table 2, Table 3, Table 4, Table 5, Table 6, Table 7 or Table 8. The substitution of a specified amino acid as defined in Table 1 shall mean the substitution of an amino acid selected from the group consisting of:

a) methionine at position 1 of part A,
b) alanine at position 2 of part A,
c) arginine at position 3 of part A,
d) threonine, valine, isoleucine or alanine at position 4 of part A,
e) lysine or arginine at position 5 of part A,
f) histidine, threonine, glutamine or lysine at position 6 of part A,
g) valine, alanine, proline, glycine, asparagine, proline, arginine, serine or histidine at position 9 of part A,
h) threonine, arginine, serine, leucine, lysine, histidine, asparagine, alanine or proline at position 10 of part A,
i) arginine, lysine, alanine, asparagine or threonine at position 11 of part A,
j) serine, alanine, threonine, leucine, lysine, arginine, aspartic acid, asparagine or glutamic acid at position 12 of part A,
k) glutamine, threonine, arginine, alanine, proline, serine, glycine, asparagine, valine, lysine or arginine at position 13 of part A,
l) proline, threonine, aspartic acid, glutamic acid, glutamine, serine, asparagine, glycine, alanine, lysine, arginine at position 14 of part A, and
m) arginine, asparagine, histidine, valine, glycine, lysine, serine, alanine, threonine, glutamic acid, proline at position 15 of part A;
n) arginine, aspartic acid, lysine, valine, glycine, proline, serine, glutamine, threonine or alanine at position 1 of part B,
o) glycine, alanine, serine, lysine, arginine, valine, threonine, proline or glutamine at position 2 of part B,
p) serine, threonine, lysine, valine, arginine, glutamine, alanine, glutamic acid, glycine, proline und aspartic acid at position 3 of part B,
q) glutamine, proline, asparagine, threonine, glutamic acid, lysine, glycine, serine, arginine, alanine or aspartic acid at position 4 of part B,
r) lysine, glutamine, proline, glycine, asparagine, threonine, histidine or arginine at position 5 of part B,
s) lysine, arginine, glutamine or histidine at position 7 of part B,
t) lysine, glutamine or arginine at position 8 of part B,
u) serine, alanine, threonine, lysine, proline or arginine at position 9 of part B,
v) tyrosine, phenylalanine, histidine, threonine, lysine, arginine, phenylalanine or glutamine at position 10 of part B,
w) arginine at position 11 of part B,
x) tyrosine, arginine, tryptophan, phenylalanine, leucine, asparagine or serine at position 12 of part B,
y) arginine or lysine at position 13 of part B, and
z) proline, alanine or serine at position 14 of part B.

The substitution of a specified amino acid as defined in Table 2 shall mean the substitution of an amino acid selected from the group consisting of:

a) glycine at position 1,
b) threonine at position 2,
c) valine at position 3,
d) alanine at position 4,
e) leucine at position 5,
f) lysine, tryptophan or arginine at position 6,
g) glutamic acid or glutamine at position 7,
h) isoleucine at position 8,
i) arginine at position 9,
j) phenylalanine, tyrosine or leucine at position 11,
k) glutamine or arginine at position 12,
l) lysine at position 13,
m) glutamine, serine or threonine at position 14, and
n) threonine, phenylalanine, tryptophan, valine, cysteine or alanine at position 15.

The substitution of a specified amino acid as defined in Table 3 shall mean the substitution of an amino acid selected from the group consisting of:
a) alanine, phenylalanine, arginine or serine at position 1,
b) alanine, methionine or serine at position 2,
c) serine, proline, threonine, alanine or cysteine at position 3,
d) phenylalanine at position 4,
e) isoleucine, valine, methionine, leucine, serine or alanine at position 5,
f) arginine at position 6,
g) glutamic acid, threonine, valine, leucine, cysteine, glutamine or alanine at position 7, h) valine or isoleucine at position 8,
i) arginine or lysine at position 9,
j) serine, glutamic acid, methionine, threonine, glutamic acid, glutamine, glycine or aspartic acid at position 10, and
k) isoleucine, valine, leucine or threonine at position 11.

The substitution of a specified amino acid as defined in Table 4 shall mean the substitution of an amino acid selected from the group consisting of:
a) threonine, serine or alanine at position 1,
b) histidine, glutamine, asparagine, alanine, tyrosine, phenylalanine, glycine, aspartic acid or glutamic acid at position 2,
c) methionine, glutamine, isoleucine, phenylalanine, tyrosine, alanine, glutamic acid, asparagine, arginine, leucine, histidine or glycine at position 3,
d) leucine, phenylalanine, valine, isoleucine or tyrosine at position 4,
e) alanine, threonine, serine, cysteine or methionine at position 5,
f) proline, asparagine, aspartic acid, arginine, alanine, threonine, phenylalanine, arginine, histidine, serine or lysine at position 6,
g) glutamine, tyrosine, aspartic acid, lysine, arginine, glutamic acid, glycine, serine, proline, histidine, asparagine or alanine at position 8,
h) isoleucine, valine or proline at position 9,
i) asparagine, glycine, threonine, glutamic acid or serine at position 10,
j) arginine or proline at position 11,
k) tryptophan or tyrosine at position 12, and
l) threonine, glutamine or serine at position 13.

The substitution of a specified amino acid as defined in Table 5 shall mean the substitution of an amino acid selected from the group consisting of:
a) alanine, proline, valine or leucine at position 1,
b) glutamic acid, aspartic acid, glutamine, histidine or leucine at position 2,
c) alanine at position 3,
d) leucine or valine at position 4,
e) valine, leucine, methionine, isoleucine, arginine, tyrosine or threonine at position 5,
f) serine or alanine at position 6,
g) isoleucine or leucine at position 7,
h) glutamine at position 8,
i) glutamic acid at position 9,
j) alanine or serine at position 10,
k) alanine or threonine at position 11,
l) glutamic acid at position 12,
m) aspartic acid, asparagine, phenylalanine, isoleucine or tyrosine at position 13,
n) tyrosine, phenylalanine or histidine at position 14,
o) leucine, isoleucine or valine at position 15,
p) valine or isoleucine at position 16,
q) glycine, arginine, glutamic acid, histidine, asparagine, threonine, glutamic acid, aspartic acid or glutamine at position 17,
r) leucine, methionine or isoleucine at position 18,
s) phenylalanine, methionine or leucine at position 19,
t) serine, glutamic acid, aspartic acid or glycine at position 20,
u) aspartic acid, methionine, valine, asparagine, glutamic acid, alanine, arginine, lysine at position 21,
v) serine, glycine, alanine or threonine at position 22,
w) methionine, tryptophan, asparagine or histidine at position 23,
x) leucine or histidine at position 24,
y) cysteine or leucine at position 25,
z) alanine or threonine at position 26,
aa) leucine or isoleucine at position 27,
bb) histidine at position 28, and
cc) alanine or serine at position 29.

The substitution of a specified amino acid as defined in Table 6 shall mean the substitution of an amino acid selected from the group consisting of:
a) arginine, lysine or histidine at position 1,
b) arginine at position 2,
c) valine or isoleucine at position 3,
d) threonine at position 4,
e) leucine, isoleucine or valine at position 5,
f) methionine or leucine at position 6, and
g) arginine, lysine, glutamine, leucine or threonine at position 7.

The substitution of a specified amino acid as defined in Table 7 shall mean the substitution of an amino acid selected from the group consisting of:
a) lysine or arginine at position 1,
b) aspartic acid at position 2,
c) phenylalanine, leucine, isoleucine, methionine or tryptophan at position 3,
d) glutamic acid, glutamine or arginine at position 4,
e) leucine at position 5,
f) alanine or threonine at position 6,
g) arginine at position 7,
h) arginine at position 8,
i) leucine or isoleucine at position 9, and
j) glycine, arginine or threonine at position 10.

The substitution of a specified amino acid as defined in Table 8 shall mean the substitution of an amino acid selected from the group consisting of:
a) glycine, lysine, alanine, serine or threonine at position 1,
b) lysine, arginine, isoleucine or alanine at position 2,
c) glycine, glutamic acid or alanine at position 3,
d) arginine, glutamine or valine at position 4, e) proline, glycine, isoleucine, glutamine, leucine, serine or histidine at position 5, and
f) tryptophan, leucine, phenylalanine or valine at position 6.

In a particularly preferred embodiment, the at least one mutation causes a substitution of a specified amino acid of SEQ ID NO: 1. Thus, the plant according to the present invention comprises at least one substitution of the specified amino acids of SEQ ID NO: 1, i.e. those amino acids which are highly conserved and named in the consensus sequence of SEQ ID NO: 1. The substitution of a specified amino acid of SEQ ID NO: 1 shall mean the substitution of an amino acid selected from group consisting of:
  a) methionine at position 1,
  b) alanine at position 2,
  c) arginine at position 3,
  d) threonine at position 4,
  e) lysine at position 5,
  f) histidine at position 6,
  g) alanine at position 9,
  h) arginine at position 10,
  i) arginine at position 11,
  j) serine at position 12,
  k) arginine at position 13,
  l) lysine at position 14, and
  m) arginine at position 15.

In a particularly preferred embodiment, the at least one mutation causes a substitution of a specified amino acid of SEQ ID NO: 2. Thus, the plant according to the present invention comprises at least one substitution of the specified amino acids of SEQ ID NO: 2, i.e. those amino acids which are highly conserved and named in the consensus sequence of SEQ ID NO: 2. The substitution of a specified amino acid of SEQ ID NO: 2 shall mean the substitution of an amino acid selected from group consisting of:
  a) glutamine at position 1,
  b) serine at position 2,
  c) glutamine at position 3,
  d) threonine at position 4,
  e) glutamine at position 5,
  f) lysine at position 7,
  g) lysine at position 8,
  h) lysine at position 9,
  i) histidine at position 10,
  j) arginine at position 11,
  k) tyrosine at position 12,
  l) arginine at position 13, and
  m) proline at position 14.

In a particularly preferred embodiment, the at least one mutation causes a substitution of a specified amino acid of SEQ ID NO: 3. Thus, the plant according to the present invention comprises at least one substitution of the specified amino acids of SEQ ID NO: 3, i.e. those amino acids which are highly conserved and named in the consensus sequence of SEQ ID NO: 3. The substitution of a specified amino acid of SEQ ID NO: 3 shall mean the substitution of an amino acid selected from group consisting of:
  a) glycine at position 1,
  b) threonine at position 2,
  c) valine at position 3,
  d) alanine at position 4,
  e) leucine at position 5,
  f) arginine at position 6,
  g) glutamic acid at position 7,
  h) isoleucine at position 8,
  i) arginine at position 9,
  j) phenylalanine at position 11,
  k) glutamine or arginine at position 12,
  l) lysine at position 13,
  m) threonine at position 14, and
  n) threonine at position 15.

In a particularly preferred embodiment, the at least one mutation causes a substitution of a specified amino acid of SEQ ID NO: 4. Thus, the plant according to the present invention comprises at least one substitution of the specified amino acids of SEQ ID NO: 4, i.e. those amino acids which are highly conserved and named in the consensus sequence of SEQ ID NO: 4. The substitution of a specified amino acid of SEQ ID NO: 4 shall mean the substitution of an amino acid selected from group consisting of:
  a) alanine at position 1,
  b) alanine at position 2,
  c) proline at position 3,
  d) phenylalanine at position 4,
  e) isoleucine at position 5,
  f) arginine at position 6,
  g) leucine acid at position 7,
  h) valine at position 8,
  i) arginine at position 9,
  j) glutamic acid at position 10, and
  k) isoleucine at position 11.

In a particularly preferred embodiment, the at least one mutation causes a substitution of a specified amino acid of SEQ ID NO: 5. Thus, the plant according to the present invention comprises at least one substitution of the specified amino acids of SEQ ID NO: 5, i.e. those amino acids which are highly conserved and named in the consensus sequence of SEQ ID NO: 5. The substitution of a specified amino acid of SEQ ID NO: 5 shall mean the substitution of an amino acid selected from group consisting of:
  a) threonine at position 1,
  b) asparagine at position 2,
  c) phenylalanine at position 3,
  d) leucine at position 4,
  e) alanine at position 5,
  f) proline at position 6,
  g) glutamic acid at position 8,
  h) valine at position 9,
  i) threonine at position 10,
  j) arginine at position 11,
  k) tryptophan at position 12, and
  l) threonine at position 13.

In a particularly preferred embodiment, the at least one mutation causes a substitution of a specified amino acid of SEQ ID NO: 6. Thus, the plant according to the present invention comprises at least one substitution of the specified amino acids of SEQ ID NO: 6, i.e. those amino acids which are highly conserved and named in the consensus sequence of SEQ ID NO: 6. The substitution of a specified amino acid of SEQ ID NO: 6 shall mean the substitution of an amino acid selected from group consisting of:
  a) alanine at position 1,
  b) glutamic acid at position 2,
  c) alanine at position 3,
  d) leucine at position 4,
  e) leucine at position 5,
  f) alanine at position 6,
  g) leucine at position 7,
  h) glutamine at position 8,
  i) glutamic acid at position 9,
  j) alanine at position 10,
  k) alanine at position 11,
  l) glutamic acid at position 12,
  m) aspartic acid at position 13, n) phenylalanine at position 14,
o) leucine at position 15,
p) valine at position 16,
q) histidine at position 17,
r) leucine at position 18,
s) phenylalanine at position 19,
t) glutamic acid at position 20,
u) aspartic acid at position 21,
v) alanine at position 22,
w) methionine at position 23,
x) leucine at position 24,
y) cysteine at position 25,
z) alanine at position 26,
aa) isoleucine at position 27,
bb) histidine at position 28, and
cc) alanine at position 29.

In a particularly preferred embodiment, the at least one mutation causes a substitution of a specified amino acid of SEQ ID NO: 7. Thus, the plant according to the present invention comprises at least one substitution of the specified amino acids of SEQ ID NO: 7, i.e. those amino acids which are highly conserved and named in the consensus sequence of SEQ ID NO: 7. The substitution of a specified amino acid of SEQ ID NO: 7 shall mean the substitution of an amino acid selected from group consisting of:
a) lysine at position 1,
b) arginine at position 2,
c) valine at position 3,
d) threonine at position 4,
e) leucine at position 5,
f) methionine at position 6, and
g) lysine at position 7.

In a particularly preferred embodiment, the at least one mutation causes a substitution of a specified amino acid of SEQ ID NO: 8. Thus, the plant according to the present invention comprises at least one substitution of the specified amino acids of SEQ ID NO: 8, i.e. those amino acids which are highly conserved and named in the consensus sequence of SEQ ID NO: 8. The substitution of a specified amino acid of SEQ ID NO: 8 shall mean the substitution of an amino acid selected from group consisting of:
a) lysine at position 1,
b) aspartic acid at position 2,
c) phenylalanine at position 3,
d) glutamic acid at position 4,
e) leucine at position 5,
f) alanine at position 6,
g) arginine at position 7,
h) arginine at position 8,
i) leucine at position 9, and
j) glycine at position 10.

In a particularly preferred embodiment, the at least one mutation causes a substitution of a specified amino acid of SEQ ID NO: 9. Thus, the plant according to the present invention comprises at least one substitution of the specified amino acids of SEQ ID NO: 9, i.e. those amino acids which are highly conserved and named in the consensus sequence of SEQ ID NO: 9. The substitution of a specified amino acid of SEQ ID NO: 9 shall mean the substitution of an amino acid selected from group consisting of:
a) glycine at position 1,
b) lysine at position 2,
c) glycine at position 3,
d) arginine acid at position 4,
e) proline at position 5, and
f) tryptophan at position 6.

In a further particularly preferred embodiment, the at least one mutation causes a substitution of a specified amino acid in the N-terminal tail domain, wherein the amino acid arginine at position 3 of SEQ ID NO: 1 is substituted, preferably for lysine, or the amino acid arginine at position 2 of SEQ ID NO: 23 is substituted, preferably for lysine, or the amino acid arginine at position 10 of SEQ ID NO: 1 is substituted, preferably for phenylalanine, or the amino acid serine at position 9 of SEQ ID NO: 14 is substituted, preferably for phenylalanine, or the amino acid arginine at position 16 of SEQ ID NO: 14 is substituted, preferably for glutamine, or the amino acid serine at position 24 of SEQ ID NO: 14 is substituted, preferably for leucine, or the amino acid serine at position 24 of SEQ ID NO: 14 is substituted, preferably for leucine, or the amino acid alanine at position 25 of SEQ ID NO: 17 is substituted, preferably for threonine, or the amino acid glutamic acid at position 29 of SEQ ID NO: 14 is substituted, preferably for lysine, or the amino acid glycine at position 30 of SEQ ID NO: 14 is substituted, preferably for aspartic acid, or the amino acid alanine at position 33 of SEQ ID NO: 14 or at position 32 of SEQ ID NO: 20 is substituted, preferably for threonine, or the amino acid proline at position 35 of SEQ ID NO: 14 is substituted, preferably for leucine, or the amino acid glutamic acid at position 35 of SEQ ID NO: 20 is substituted, preferably for lysine, or the amino acid serine at position 41 of SEQ ID NO: 14 is substituted, preferably for asparagine, or the amino acid glycine at position 43 of SEQ ID NO: 14 is substituted, preferably for glutamic acid, or the amino acid proline at position 50 of SEQ ID NO: 14 is substituted, preferably for serine, or the amino acid proline at position 55 of SEQ ID NO: 14 is substituted, preferably for leucine, or the amino acid glycine at position 57 of SEQ ID NO: 14 is substituted, preferably for aspartic acid, or the amino acid glycine at position 61 of SEQ ID NO: 14 is substituted, preferably for glutamic acid, or the amino acid arginine at position 65 of SEQ ID NO: 14 is substituted, preferably for glutamine, or the amino acid arginine at position 65 of SEQ ID NO: 14 is substituted, preferably for stop signal, or the amino acid proline at position 71 of SEQ ID NO: 14 is substituted, preferably for serine, or the amino acid aspartic acid at position 46 of SEQ ID NO: 23 is substituted, preferably for asparagine or glycine, or the amino acid lysine at position 7 of SEQ ID NO: 2 is substituted, preferably for serine, or the amino acid proline at position 56 of SEQ ID NO: 20 is substituted, preferably for serine, or the amino acid proline at position 14 of SEQ ID NO: 2 is substituted, preferably for valine, or the amino acid alanine at position 62 of SEQ ID NO: 17 is substituted, preferably for valine.

In a further particularly preferred embodiment, the at least one mutation causes a substitution of a specified amino acid in the αN-helix, wherein the amino acid threonine at position 2 of SEQ ID NO: 3 is substituted, preferably for serine, or the amino acid threonine at position 64 of SEQ ID NO: 17 is substituted, preferably for serine.

In a further particularly preferred embodiment, the at least one mutation causes a substitution of a specified amino acid in the α1-helix, wherein the amino acid alanine at position 1 of SEQ ID NO: 4 is substituted, preferably for threonine, or the amino acid alanine at position 105 of SEQ ID NO: 14 is substituted, preferably for threonine, or the amino acid arginine at position 6 of SEQ ID NO: 4 is substituted, preferably for glutamine, or the amino acid arginine at position 110 of SEQ ID NO: 14 is substituted, preferably for glutamine, or the amino acid valine at position 89 of SEQ ID NO: 20 is substituted, preferably for methionine, or the amino acid glutamic acid at position 10 of SEQ ID NO: 4 is substituted, preferably for asparagine, or the amino acid serine at position 114 of SEQ ID NO: 14 is substituted, preferably for asparagine.

In a further particularly preferred embodiment, the at least one mutation causes a substitution of a specified amino acid in the loop1, wherein the amino acid asparagine at position 2 of SEQ ID NO: 5 is substituted, preferably for valine, or the amino acid alanine at position 95 of SEQ ID NO: 17 is substituted, preferably for valine, or the amino acid proline at position 6 of SEQ ID NO: 5 is substituted, preferably for serine, or the amino acid proline at position 121 of SEQ ID NO: 14 is substituted, preferably for serine, or the amino acid tryptophan at position 12 of SEQ ID NO: 5 is substituted, preferably for a stop signal, or the amino acid tryptophan at position 127 of SEQ ID NO: 14 is substituted, preferably for a stop signal.

In a further particularly preferred embodiment, the at least one mutation causes a substitution of a specified amino acid in the α2-helix, wherein the amino acid alanine at position 1 of SEQ ID NO: 6 is substituted, preferably for threonine, or the amino acid alanine at position 107 of SEQ ID NO: 20 is substituted, preferably for threonine, or the amino acid leucine at position 4 of SEQ ID NO: 6 is substituted, preferably for phenylalanine or glutamine, or the amino acid leucine at position 132 of SEQ ID NO: 14 or position 106 of SEQ ID NO: 23 is substituted, preferably for phenylalanine or glutamine, or the amino leucine at position 7 of SEQ ID NO: 6 is substituted, preferably for proline, or the amino acid leucine at position 109 of SEQ ID NO: 23 is substituted, preferably for proline, or the amino acid glutamine at position 8 of SEQ ID NO: 6 is substituted, preferably for a stop signal or leucine, or the amino acid glutamine at position 114 of SEQ ID NO: 20 or position 110 of SEQ ID NO: 23 is substituted, preferably for a stop signal or leucine, or the amino acid alanine at position 10 of SEQ ID NO: 6 is substituted, preferably for threonine, or the amino acid alanine at position 138 of SEQ ID NO: 14 is substituted, preferably for threonine, or the amino acid cysteine at position 25 of SEQ ID NO: 6 is substituted, preferably for tyrosine, or the amino acid cysteine at position 153 of SEQ ID NO: 14 is substituted, preferably for tyrosine, or the amino acid alanine at position 26 of SEQ ID NO: 6 is substituted, preferably for valine, or the amino acid alanine at position 154 of SEQ ID NO: 14 is substituted, preferably for valine. In a further particularly preferred embodiment, the at least one mutation causes a substitution of a specified amino acid in the loop2, wherein the amino acid arginine at position 2 of SEQ ID NO: 7 is substituted, preferably for histidine, or the amino acid arginine at position 159 of SEQ ID NO: 14 is substituted, preferably for histidine, or the amino acid valine at position 3 of SEQ ID NO: 7 is substituted, preferably for isoleucine, or the amino acid valine at position 160 of SEQ ID NO: 14 is substituted, preferably for isoleucine, or the amino acid threonine at position 4 of SEQ ID NO: 7 is substituted, preferably for isoleucine, or the amino acid threonine at position 139 of SEQ ID NO: 20 is substituted, preferably for isoleucine.

In a further particularly preferred embodiment, the at least one mutation causes a substitution of a specified amino acid in the α3-helix, wherein the amino acid aspartic acid at position 2 of SEQ ID NO: 8 is substituted, preferably for asparagine, or the amino acid aspartic acid at position 166 of SEQ ID NO: 14 is substituted, preferably for asparagine, or the amino acid glutamic acid at position 4 of SEQ ID NO: 8 is substituted, preferably for lysine, or the amino acid glutamic acid at position 168 of SEQ ID NO: 14 is substituted, preferably for lysine, or the amino acid arginine at position 8 of SEQ ID NO: 8 is substituted, preferably for histidine, or the amino acid arginine at position 172 of SEQ ID NO: 14 is substituted, preferably for histidine, or the amino acid leucine at position 9 of SEQ ID NO: 8 is substituted, preferably for phenylalanine, or the amino acid leucine at position 173 of SEQ ID NO: 14 is substituted, preferably for phenylalanine, or the amino acid glycine at position 10 of SEQ ID NO: 8 is substituted, preferably for glutamic acid, or the amino acid glycine at position 174 of SEQ ID NO: 14 or position 152 of SEQ ID NO: 20 is substituted, preferably for glutamic acid.

In a further particularly preferred embodiment, the at least one mutation causes a substitution of a specified amino acid in the C-terminal domain, wherein the amino acid glycine at position 3 of SEQ ID NO: 9 is substituted, preferably for histidine, or the amino acid arginine at position 155 of SEQ ID NO: 20 is substituted, preferably for histidine, or the amino acid arginine at position 4 of SEQ ID NO: 9 is substituted, preferably for lysine, or the amino acid arginine at position 178 of SEQ ID NO: 14 is substituted, preferably for lysine, or the amino acid serine at position 157 of SEQ ID NO: 17 is substituted, preferably for leucine.

In an alternative preferred embodiment, the at least one mutation is positioned in a splicing site of the genomic nucleotide sequence encoding the CENH3 protein and/or the at least one mutation creates a new splicing site within an exon. Preferably, a plant which is heterozygous for such mutation(s) is viable. Such mutation(s) can cause a malfunctioning splicing site (splicing error), which then results in an increased cellular translational production of non-fully functional CENH3 proteins, which show e.g. an impaired stability, a reduced binding affinity to DNA, a changed geometric shape of the protein, preferably a changed secondary or tertiary structure, or a disordered protein folding compared to the fully functional wildtype CENH3 protein.

In a particularly preferred embodiment, the at least one mutation causes a splicing error, preferably in intron 1 of SEQ ID NO: 12, leading to an alteration of the amino acid sequence of the CENH3 protein of *Brassica napus* after amino acid at position 18 of SEQ ID NO: 14, a splicing error, preferably in intron 2 of SEQ ID NO: 12, leading to an alteration of the amino acid sequence of the CENH3 protein of *Brassica napus* after amino acid at position 33 of SEQ ID NO: 14, a splicing error, preferably in exon 3 of SEQ ID NO: 12, leading to an alteration of the amino acid sequence of the CENH3 protein of *Brassica napus* after amino acid at position 37 of SEQ ID NO: 14, or a splicing error, preferably in intron 8 of SEQ ID NO: 12, leading to an alteration of the amino acid sequence of the CENH3 protein of *Brassica napus* after amino acid at position 163 of SEQ ID NO: 14, or the at least one mutation causes a splicing error, preferably in intron 4 of SEQ ID NO: 18, leading to an alteration of the amino acid sequence of the CENH3 protein of *Zea mays* after amino acid at position 89 of SEQ ID NO: 20, a splicing error, preferably in intron 5 of SEQ ID NO: 18, leading to an alteration of the amino acid sequence of the CENH3 protein of *Zea mays* after amino acid at position 115 of SEQ ID NO: 20, or a splicing error, preferably in intron 6 of SEQ ID NO: 18, leading to an alteration of the amino acid sequence of the CENH3 protein of *Zea mays* after amino acid at position 141 of SEQ ID NO: 20, or the at least one mutation causes a splicing error, preferably in intron 1 of SEQ ID NO: 15, leading to an alteration of the amino acid sequence of the CENH3 protein of *Sorghum bicolor* after amino acid at position 26 of SEQ ID NO: 17.

In an additional alternative preferred embodiment, the at least one mutation causes an alteration of the amino acid sequence of the CENH3 protein and said alteration confers the biological activity of a haploid inducer, wherein the alteration is an insertion or deletion of one or more amino acids. The insertion can be introduced for instances by transposon mutagenesis and deletion can be created for instances by genomic engineering. Insertion and deletion can occur in any nucleotide sequence encoding one of the above described segments, in a nucleotide sequence of an intron or in a nucleotide sequence of the 5' untranslated region (UTR) or 3' UTR of the CENH3 gene, wherein the 5' UTR is located upstream from the nucleotide sequence encoding the N terminal tail domain and the 3' UTR is located downstream from the nucleotide sequence encoding the C-terminal domain. In any case the Insertion or deletion causes an alteration of the amino acid sequence of the CENH3 protein and said alteration confers the biological activity of a haploid inducer. The insertion can have a length of at least 1 nucleotide, at least 2 nucleotides, at least 3 nucleotides, at least 4 nucleotides, at least 5 nucleotides, at least 6 nucleotides, at least 7 nucleotides, at least 8 nucleotides, at least 9 nucleotides, at least 10 nucleotides, at least 12 nucleotides, at least 14 nucleotides, at least 16 nucleotides, at least 18 nucleotides, at least 20 nucleotides, at least 25 nucleotides, at least 30 nucleotides, at least 40 nucleotides, at least 50 nucleotides, at least 75 nucleotides, at least 100 nucleotides, at least 200 nucleotides, at least 300 nucleotides, or at least 500 nucleotides.

In the context of the present invention the term 'at least one mutation' refers to preferably one mutation, in particular solely one mutation. In a further preferred embodiment, the term 'at least one mutation' refers to two mutations, in particular solely two mutations. In a further preferred embodiment, the term 'at least one mutation' refers to three mutations, in particular solely three mutations. In a further preferred embodiment, the term 'at least one mutation' refers to four mutations, in particular solely four mutations. In a further preferred embodiment, the term 'at least one mutation' refers to five mutations, in particular solely five mutations. In case of more than one mutation, mutations can occur also in different polynucleotides and causes alteration of the amino acid sequences of different CENH3 protein if existing for the specific plant species. For example, *Hordeum vulgare* have two different CENH3 proteins.

In a preferred embodiment of the present invention, the at least one mutation is at least one mutation, is at least two mutations, is at least three mutations, is at least four mutations or is at least five mutations.

In a furthermore preferred embodiment, in one segment of the CENH3 protein one amino acid substitution, in particular solely one amino acid substitution, is present.

In a furthermore preferred embodiment, in one segment of the CENH3 protein two amino acid substitutions, in particular solely two amino acid substitutions, are present.

In a furthermore preferred embodiment, in one segment of the CENH3 protein three amino acid substitutions, in particular solely three amino acid substitutions, are present.

In a furthermore preferred embodiment, in one segment of the CENH3 protein four amino acid substitutions, in particular solely four amino acid substitutions, are present.

In a furthermore preferred embodiment, in one segment of the CENH3 protein five amino acid substitutions, in particular solely five amino acid substitutions, are present.

In a preferred embodiment of the present invention, in one segment of the CENH3 protein 1, 1 or 2, 1 to 3, 1 to 4, 1 to 5, preferably 1 to 6, and more preferably 1 to 7 amino acid substitutions are present.

In particular, the present invention is concerned partly with mutations that cause or lead to an amino acid substitution within a segment of the CENH3 protein. Tus, in this context a mutation preferably is a non-synonymous point mutation or substitution in the DNA sequence encoding the CENH3 protein resulting in a change in amino acid. This is also called a missense mutation. Further, the change in amino acid or the amino acid substitution may be conservative, i.e. a change to an amino acid with similar physiochemical properties, semi-conservative, e.g. negative to positively charged amino acid, or radical, i.e. a change to a vastly different amino acid.

In a preferred embodiment of the present invention, the present plant having biological activity of a haploid inducer is homozygous with respect to the at least one mutation. In a further embodiment of the present invention, the present plant having biological activity of a haploid inducer is heterozygous with respect to the at least one mutation.

The plant according to the present invention has the biological activity of a haploid inducer. This means that crossing between the plant according to the present invention and a wildtype plant or a plant expressing wildtype CENH3 protein yields at least 0.1%, 0.2%, 0.3%, 0.4%, 0.5%, 0.6%, 0.7%, 0.8%, 0.9%, preferably at least 1%, preferably at least 2%, preferably at least 3%, preferably at least 4%, preferably at least 5%, preferably at least 6%, preferably at least 7%, preferably at least 8%, preferably at least 9%, most preferred at least 10%, at least 15%, at least 20% or more haploid progeny. Thereby, a wildtype plant is preferably a plant of the same species which does not comprise the at least one mutation of the plant according to the present invention within the corresponding endogenous CENH3 gene, i.e. the plant is able to express the native CENH3 protein, and a plant expressing wildtype CENH3 is preferably a plant of the same species which comprises i) a polynucleotide comprising a nucleotide sequence encoding the CENH3 protein without the at least one mutation of the plant according to the present invention and is able to express said native CENH3 protein or ii) a polynucleotide comprising a nucleotide sequence encoding a CENH3 protein from another plant species that shows a comparable functionality to the native CENH3, for instance, such CENH3 protein derived from another plant species can be introduced as a transgene.

Thus, the present invention most advantageously provides means and methods to generate haploid inducer lines in a wide range of eudicot, dicot and monocot species. The present invention also allows the exchange of maternal cytoplasm and to create for instance cytoplasmic male sterility plants with a desired genotype in a single process step. The present invention is advantageous insofar as a single amino acid mutation can be generated by mutagenesis or any other non-GMO-based approaches.

Thus, the entire process of haploidization via application of a haploid inducer line characterized by a mutated endogenous CENH3 gene with an alteration of the amino acid at at least one of the positions provided by the present invention is non-transgenic in a preferred embodiment.

In the context of the present invention, an "endogenous" gene, allele or protein refers to a non-recombinant sequence of a plant as the sequence occurs in the respective plant, in particular wildtype plant. The term "mutated" refers to a human-altered sequence. Examples of human-induced non-transgenic mutation include exposure of a plant to a high dose of chemical, radiological, or other mutagen for the purposes of selecting mutants. Alternatively, human-induced transgenic mutations, i.e. recombinant alterations or genomic engineering for example by means of TALE nucleases, zinc-finger nucleases or a CRISPR/Cas system, include fusions, insertions, deletions, and/or changes to the DNA or amino acid sequence.

A polynucleotide or polypeptide sequence is "heterologous or exogenous to" an organism if it originates from a foreign species, or, if from the same species, is modified from its original form. "Recombinant" refers to a human-altered, i.e. transgenic polynucleotide or polypeptide sequence. A "transgene" is used as the term is understood in the art and refers to a, preferably heterologous, nucleic acid introduced into a cell by human molecular manipulation of the cell's genome, e.g. by molecular transformation. Tus, a "transgenic plant" is a plant comprising a transgene, i.e. is a genetically-modified plant. The transgenic plant can be the initial plant into which the transgene was introduced as well as progeny thereof whose genome contains the transgene as well.

The term 'nucleotide sequence encoding' refers to a nucleic acid which directs the expression of a specific protein, in particular the CENH3 protein or parts thereof. The nucleotide sequences include both the DNA strand sequence that is transcribed into RNA and the RNA sequence that is translated into the protein. The nucleotide sequences include both the full length nucleic acid sequences as well as non-full length sequences derived from the full length sequences.

The term 'gene' refers to a coding nucleotide sequence and associated regulatory nucleotide sequences, intron(s), 5' UTR and/or 3' UTR.

The term 'regulatory element' refers to a sequence, preferably a nucleotide sequence, located upstream (5'), within and/or downstream (3') to a nucleotide sequence, preferably a coding sequence, whose transcription and expression is controlled by the regulatory element, potentially in conjunction with the protein biosynthetic apparatus of the cell. 'Regulation' or 'regulate' refer to the modulation of the gene expression induced by DNA sequence elements located primarily, but not exclusively upstream (5) from the transcription start of the gene of interest. Regulation may result in an all or none response to a stimulation, or it may result in variations in the level of gene expression.

A regulatory element, in particular DNA sequence, such as a promoter is said to be "operably linked to" or "associated with" a DNA sequence that codes for a RNA or a protein, if the two sequences are situated and orientated such that the regulatory DNA sequence effects expression of the coding DNA sequence.

A 'promoter' is a DNA sequence initiating transcription of an associated DNA sequence, in particular being located upstream (5') from the start of transcription and being involved in recognition and being of the RNA-polymerase. Depending on the specific promoter region it may also include elements that act as regulators of gene expression such as activators, enhancers, and/or repressors.

A '3' regulatory element' (or '3' end') refers to that portion of a gene comprising a DNA segment, excluding the 5' sequence which drives the initiation of transcription and the structural portion of the gene, that determines the correct termination site and contains a polyadenylation signal and any other regulatory signals capable of effecting messenger RNA (mRNA) processing or gene expression. The polyadenylation signal is usually characterized by effecting the addition of polyadenylic acid tracts to the 3' end of the mRNA precursor. Polyadenylation signals are often recognized by the presence of homology to the canonical form 5'-AATAAA-3'.

The term 'coding sequence' refers to that portion of a gene encoding a protein, polypeptide, or a portion thereof, and excluding the regulatory sequences which drive the initiation or termination of transcription.

The gene, coding sequence or the regulatory element may be one normally found in the cell, in which case it is called 'autologous' or 'endogenous', or it may be one not normally found in a cellular location, in which case it is termed 'heterologous', 'transgenic' or 'transgene'.

A 'heterologous' gene, coding sequence or regulatory element may also be autologous to the cell but is, however, arranged in an order and/or orientation or in a genomic position or environment not normally found or occurring in the cell in which it is transferred.

The term 'vector' refers to a recombinant DNA construct which may be a plasmid, virus, autonomously replicating sequence, an artificial chromosome, such as the bacterial artificial chromosome BAC, phage or other nucleotide sequence, in which at least two nucleotide sequences, at least one of which is a nucleic acid molecule of the present invention, have been joined or recombined. A vector may be linear or circular. A vector may be composed of a single or double stranded DNA or RNA.

The term 'expression' refers to the transcription and/or translation of an endogenous gene or a transgene in plants.

'Transformation', 'transforming' and 'transferring' refers to methods to transfer nucleic acid molecules, in particular DNA, into cells including, but not limited to, biolistic approaches such as particle bombardment, microinjection, permeabilising the cell membrane with various physical, for instance electroporation, or chemical treatments, for instance polyethylene glycol or PEG, treatments; the fusion of protoplasts or *Agrobacterium tumefaciens* or *rhizogenes* mediated trans-formation. For the injection and electroporation of DNA in plant cells there are no specific requirements for the plasmids used. Plasmids such as pUC derivatives can be used. If whole plants are to be regenerated from such transformed cells, the use of a selectable marker is preferred. Depending upon the method for the introduction of desired genes into the plant cell, further DNA sequences may be necessary; if, for example, the Ti or Ri plasmid is used for the transformation of the plant cell, at least the right border, often, however, the right and left border of the Ti and Ri plasmid T-DNA have to be linked as flanking region to the genes to be introduced. Preferably, the transferred nucleic acid molecules are stably integrated in the genome or plastome of the recipient plant.

In the context of the present invention the term 'biological activity of a haploid inducer' or 'haploid inducer' or 'haploid inducer line' refers to a plant or plant line having the capability to produce haploid progeny or offspring in at least 0.1%, at least 0.2%, 0.3%, 0.4%, 0.5%, 0.6%, 0.7%, 0.8%, 0.9%, preferably at least 1%, preferably at least 2%, preferably at least 3%, preferably at least 4%, preferably at least 5%, preferably at least 6%, preferably at least 7%, preferably at least 8%, preferably at least 9%, most preferred at least 10%, most preferred at least 15%, most preferred at least 20% of cases when crossed to a wildtype plant or a plant at least expressing wildtype CENH3 protein. Since the chromosomes of the haploid inducer are eliminated during meiosis the resulting haploid progeny only comprises the chromosomes of the wildtype parent. However, in case the haploid inducer was the ovule parent of the cross, the haploid progeny possesses the cytoplasm of the inducer and the chromosomes of the wildtype parent.

The term 'plant' according to the present invention includes whole plants or parts of such a whole plant.

Whole plants preferably are seed plants, or a crop. Parts of a plant are e.g. shoot vegetative organs/structures, e.g., leaves, stems and tubers; roots, flowers and floral organs/structures, e.g. bracts, sepals, petals, stamens, carpels, anthers and ovules; seed, including embryo, endosperm, and seed coat; fruit and the mature ovary; plant tissue, e.g. vascular tissue, ground tissue, and the like; and cells, e.g. guard cells, egg cells, trichomes and the like; and progeny of the same.

In any case, the plant of the present invention comprises at least one cell comprising a polynucleotide which comprises a nucleotide sequence encoding a centromeric histone H3 (CENH3) protein, wherein the polynucleotide comprises at least one mutation causing an alteration of the amino acid sequence of the CENH3 protein and said alteration confers the biological activity of a haploid inducer, preferably as specified herein in more detail. Most preferably, most or in particular all cells of the plant of the present invention comprises the mutation(s) as described herein.

The species of plants that can be used in the method of the invention are preferably eudicot, dicot and monocot plants.

The term 'plant' in a preferred embodiment relates solely to a whole plant, i.e. a plant exhibiting the full phenotype of a developed plant and capable of reproduction, a developmental earlier stage thereof, e.g. a plant embryo, or to both.

In an embodiment of the present invention the term 'plant' refers to a part of a whole plant, in particular plant material, plant cells or plant cell cultures.

The term 'plant cell' describes the structural and physiological unit of the plant, and comprises a protoplast and a cell wall. The plant cell may be in form of an isolated single cell, such as a stomatal guard cells or a cultured cell, or as a part of a higher organized unit such as, for example, a plant tissue, or a plant organ.

The term 'plant material' includes plant parts, in particular plant cells, plant tissue, in particular plant propagation material, preferably leaves, stems, roots, emerged radicles, flowers or flower parts, petals, fruits, pollen, pollen tubes, anther filaments, ovules, embryo sacs, egg cells, ovaries, zygotes, embryos, zygotic embryos per se, somatic embryos, hypocotyl sections, apical meristems, vascular bundles, pericycles, seeds, roots, cuttings, cell or tissue cultures, or any other part or product of a plant.

Thus, the present invention also provides plant propagation material of the plants of the present invention. Said "plant propagation material" is understood to be any plant material that may be propagated sexually or asexually in vivo or in vitro. Particularly preferred within the scope of the present invention are protoplasts, cells, calli, tissues, organs, seeds, embryos, pollen, egg cells, zygotes, together with any other propagating material obtained from transgenic plants. Parts of plants, such as for example flowers, stems, fruits, leaves, roots originating in mutated plants or their progeny previously mutated, preferably transformed, by means of the methods of the present invention and therefore consisting at least in part of mutated cells, are also an object of the present invention.

Preferably, the plant according to the present invention is selected from the group consisting of barley (*Hordeum vulgare*), sorghum (*Sorghum bicolor*), rye (*Secale cereale*), Triticale, sugar cane (*Saccharum officinarium*), maize (*Zea mays*), foxtail millet (*Setaria italic*), rice (*Oryza sativa*), *Oryza minuta*, *Oryza australiensis*, *Oryza alta*, wheat (*Triticum aestivum*), *Triticum durum*, *Hordeum bulbosum*, purple false brome (*Brachypodium distachyon*), sea barley (*Hordeum marinum*), goat grass (*Aegilops tauschii*), apple (*Malus domestica*), *Beta vulgaris*, sunflower (*Helianthus annuus*), Australian carrot (*Daucus glochidiatus*), American wild carrot (*Daucus pusillus*), *Daucus muricatus*, carrot (*Daucus carota*), eucalyptus (*Eucalyptus grandis*), *Erythranthe guttata*, *Genlisea aurea*, woodland tobacco (*Nicotiana sylvestris*), tobacco (*Nicotiana tabacum*), *Nicotiana tomentosiformis*, tomato (*Solanum lycopersicum*), potato (*Solanum tuberosum*), coffee (*Coffea canephora*), grape vine (*Vitis vinfera*), cucumber (*Cucumis sativus*), mulberry (*Morus notabilis*), thale cress (*Arabidopsis thaliana*), *Arabidopsis lyrata*, sand rock-cress (*Arabidopsis arenosa*), *Crucihimalaya himalaica*, *Crucihimalaya wallichii*, wavy bittercress (*Cardamine flexuosa*), peppergrass (*Lepidium virginicum*), sheperd's-purse (*Capsella bursa-pastoris*), *Olmarabidopsis pumila*, hairy rockcress (*Arabis hirsuta*), rape (*Brassica napus*), broccoli (*Brassica oleracea*), *Brassica rapa*, *Brassica juncacea*, black mustard (*Brassica nigra*), radish (*Raphanus sativus*), *Eruca vesicaria sativa*, orange (*Citrus sinensis*), *Jatropha curcas*, *Glycine max*, and black cottonwood (*Populus trichocarpa*).

Particularly preferred the plant is selected from the group consisting of barley (*Hordeum vulgare*), sorghum (*Sorghum bicolor*), rye (*Secale cereale*), Triticale, sugar cane (*Saccharum officinarium*), maize (*Zea mays*), rice (*Oryza sativa*), wheat (*Triticum aestivum*), *Triticum durum*, *Avena sativa*, *Hordeum bulbosum*, *Beta vulgaris*, sunflower (*Helianthus annuus*), carrot (*Daucus carota*), tobacco (*Nicotiana tabacum*), tomato (*Solanum lycopersicum*), potato (*Solanum tuberosum*), coffee (*Coffea canephora*), grape vine (*Vitis vinifera*), cucumber (*Cucumis sativus*), thale cress (*Arabidopsis thaliana*), rape (*Brassica napus*), broccoli (*Brassica oleracea*), *Brassica rapa*, *Brassica juncacea*, black mustard (*Brassica nigra*), radish (*Raphanus sativus*), and *Glycine max*.

The plant according to the present invention contains in a preferred embodiment the polynucleotide which comprises the nucleotide sequence encoding the CENH3 either as an endogenous gene or a transgene.

The invention relates in a preferred embodiment to a plant according to the present teaching, wherein the at least one amino acid substitution is introduced into the nucleotide sequence encoding CENH3 non-transgenically or transgenically.

Thus, preferably in an embodiment, wherein the at least one mutation is effected in the endogenous CENH3 gene, the obtained plant is non-transgenic. Preferably, the mutation is effected via non-transgenic mutagenesis, transposon mutagenesis, in particular chemical mutagenesis, preferably via EMS (ethylmethane sulfonate)-induced TILLING or targeted genome editing.

Thus, the present invention relates to a plant, wherein the non-transgenic introduction of the at least one mutation causing an alteration of the amino acid sequence of the CENH3 protein and said alteration confers the biological activity of a haploid inducer is effected via chemical mutagenesis, in particular via TILLING.

In another preferred embodiment, the at least one mutation is introduced into the plant in form of a transgene. Preferably, this is done by transforming a vector comprising a polynucleotide which comprises a nucleotide sequence encoding at least segment of CENH3 protein comprising at least one alteration of the amino acid sequence, preferably such as described herein. Methods for transformation of a plant and introducing a transgene into the genome of a plant are well-known in the prior art.

Thus, in a preferred embodiment a plant is provided, wherein the transgenic introduction of the alteration into the amino acid sequence of the CENH3 protein is effected via transformation of a vector comprising polynucleotide which comprises a nucleotide sequence encoding at least segment of CENH3 protein or the CADT domain of the CENH3 protein comprising at least one alteration of the amino acid sequence, preferably comprising at least one amino acid substitution of one of the specified amino acids of consensus sequence SEQ ID NO: 1, 2, 3, 4, 5, 6, 7, 8 or 9, or as defined in Table 1, Table 2, Table 3, Table 4, Table 5, Table 6, Table 7 or Table 8.

Preferably, the *Agrobacterium* mediated transformation, floral dip method or particle bombardment are used for transformation.

In the preferred embodiment, wherein the polynucleotide comprising the nucleotide sequence encoding the altered CENH3 protein according to the present invention is transformed into the plant in form of a transgene and one or two alleles of the endogenous CENH3 gene are preferably inactivated or knocked out. Another preferred embodiment, wherein the polynucleotide comprising the nucleotide sequence encoding the altered amino acid sequence of CENH3 protein according to the present invention is transformed into the plant in form of a transgene and the transgene is overexpressed in order to be more competitive as the endogenous CENH3 protein and preferred during generation of a kinetochore complex.

The present invention also provides a plant obtainable, in particular obtained, by a method according to the present invention and which is characterized by having the biological activity of a haploid inducer.

In a preferred embodiment of the present invention, the method of producing the plant having biological activity of a haploid inducer according to the present invention is not an essentially biological method.

Further, the present invention also provides a method of generating the plant having biological activity of a haploid inducer according to the present invention, comprising the steps of:
  i) subjecting seeds of a plant to a sufficient amount of the mutagen ethylmethane sulfonate (EMS) to obtain M1 plants,
  ii) allowing sufficient production of fertile M2 plants,
  iii) isolating genomic DNA of M2 plants and
  iv) selecting individuals possessing at least mutation causing an alteration of the amino acid sequence of CENH3.

The present invention further relates in a preferred embodiment to a method of generating a plant having biological activity of a haploid inducer according to the present invention, comprising the steps of:
  xx) providing a vector comprising polynucleotide which comprises a nucleotide sequence encoding at least a segment of amino acid sequence of a CENH3 protein, wherein the polynucleotide comprises at least one mutation causing an alteration of the amino acid sequence of the CENH3 protein,
  yy) transforming a plant cell with the vector, wherein preferably the plant cell comprising one or two endogenous alleles of a CENH3 gene inactivated or knocked out, and
  zz) regenerating a plant having the biological activity of a haploid inducer from the plant cell.

The present invention further relates in a preferred embodiment to a method of generating a plant having biological activity of a haploid inducer according to the present invention, comprising the steps of:
  yy) transforming a plant cell with a polynucleotide which comprises a nucleotide sequence encoding at least a segment of amino acid sequence of a CENH3 protein, wherein the polynucleotide comprises at least one mutation causing an alteration of the amino acid sequence of the CENH3 protein or a vector comprising polynucleotide which comprises a nucleotide sequence encoding at least a segment of amino acid sequence of a CENH3 protein, wherein the polynucleotide comprises at least one mutation causing an alteration of the amino acid sequence of the CENH3 protein, and
  zz) regenerating a plant having the biological activity of a haploid inducer from the plant cell.

In particular, the present invention relates to a haploid plant, obtainable, in particular obtained, by:
  a) a cross of a plant having the biological activity of a haploid inducer according to the present invention with a plant expressing wildtype CENH3 protein, and optionally
  b) identifying haploid progeny generated from the crossing step.

Preferably, the identified haploid plant can be converted into a double haploid plant, preferably via colchicine treatment, which is also part of the present invention. Tus, the present invention also relates to a double-haploid plant, obtainable, in particular obtained, by converting the haploid plant according to the present invention into a double haploid plant, preferably via colchicine treatment or via spontaneous chromosome doubling.

Thus, the present invention provides also a method of generating a haploid plant, comprising the steps of:
  a) crossing a plant having the biological activity of a haploid inducer according to the present invention to a plant expressing wildtype CENH3 protein and
  b) identifying haploid progeny generated from the crossing step.

In a further step c) the selected haploid plant is preferably converted into a double haploid plant, preferably via colchicine treatment. Tus, the invention relates also to a method of generating a double haploid plant.

In a preferred embodiment of the present invention, the method provided is not an essentially biological method.

In particular, the present methods do not rely solely on, in particular do not consist of, natural phenomena such as crossing or selection, but in fact are essentially based on the technical teaching so as to provide a specifically mutated nucleotide sequence prepared by mankind's contribution. Thus, the present invention introduces a specific structural feature, namely a mutation, into a nucleotide sequence and a plant of the present invention, which mutation is not caused by or associated with any natural phenomena such as crossing or selection.

In a particular embodiment of the present invention, which provides a method including a crossing step, said crossing step does not provide—such as a crossing usually does—heterozygous progeny but in fact homozygous progeny. Furthermore, the haploidy of progeny is not the result of the mixing of genes of the plants used for sexual crossing.

Furthermore, the presently claimed process of generating a double haploid plant cannot be found in nature.

Further, the present invention also provides a method of facilitating a cytoplasm exchange, comprising the steps of:
x) crossing a plant according to the present invention as ovule parent to a plant expressing wildtype CENH3 protein as pollen parent, and
y) obtaining a haploid progeny plant comprising the chromosomes of the pollen parent and the cytoplasm of ovule parent.

In a preferred embodiment of the present invention, the method provided is not an essentially biological method. Said method is not a biological method essentially for the same reasons as indicated above, in particular since it is not entirely made up of natural phenomena such as crossing and selection, but involves as an essential feature a significant technical teaching so as to provide a particular mutation in a nucleotide sequence and a plant of the present invention. Furthermore, the haploidy of the progeny is not the result of the mixing of genes of the plants used for sexual crossing.

The method can advantageously be used to create cytoplasmic male sterility (CMS). CMS is caused by the extranuclear genome (mitochondria or chloroplasts) and shows maternal inheritance. Tus, the plant according to the present invention has to exhibit CMS and be the ovule parent of the cross. In this way CMS can be introduced into the crossing partner, preferably being an elite line of a crop.

In a preferred embodiment, the plant according to the present invention can also be used in a method to restore male fertility by providing a normal cytoplasm to a crossing partner that is CMS. Trough such a cross the chromosomes of the CMS plant are introduced into the normal cytoplasm of the haploid inducer of the present invention which is not CMS. However, pollen production of the CMS plant has to be induced via temperature, light, length of day etc.

Without being bound by theory a possible model of how the present methods, in particular a method of uniparental chromosome elimination, works in inducer CENH3×wild type CENH3 interspecific hybrid embryos could work as follows: (A) Likely haploid inducer-derived egg cells contain either less CENH3 or compared to wild type a reduced unknown 'CENH3-transgeneration required signature'. A reduced amount of maternal CENH3 is less likely as according to studies performed with a CENH3-GFP reporter in *A. thaliana* plants sperm nuclei but not eggs cells are marked by CENH3. However, it is still possible that residual maternal CENH3s, generating a 'centromeric imprinting' are transmitted to the progeny. (B) Within a few hours after fertilization also paternal wild type CENH3 is actively removed from the zygote nucleus, and (C) centromeric reloading of CENH3-GFP in the zygote occurs at the 16-nuclei stage of endosperm development in *A. thaliana*. (D) In embryos undergoing haploidization centromeric reloading of the maternal chromosomes is impaired or delayed causing lagging chromosomes because of centromere inactivity during anaphase. Subsequently micronucleated haploid inducer chromosomes will degrade and (E) a haploid embryo will develop. Haploid embryos contain paternal-derived chromosomes in the background of maternal-derived cytoplasm.

The present invention also relates to a polynucleotide which comprises a nucleotide sequence encoding at least a segment of amino acid sequence of a CENH3 protein or a CENH3 protein, wherein the polynucleotide comprises at least one mutation causing an alteration of the amino acid sequence of the CENH3 protein.

The present invention also relates to a vector, in particular viral vector, construct or plasmid comprising said polynucleotide and, if present, associates sequences, preferably as indicated herein.

In a particularly preferred embodiment of the present invention, the polynucleotide which comprises the nucleotide sequence encoding a segment of the CENH3 protein preferably comprises at least the complete coding region of CENH3, in particular the gene of CENH3.

In a furthermore preferred embodiment of the present invention, polynucleotide or the coding sequence of the CENH3 may be associated with regulatory elements, such as 5'- and/or 3'-regulatory elements, most preferably with a promoter, preferably a constitutive or inducible promoter.

Further, a plant cell comprising said polynucleotide or a vector comprising it as a transgene is provided by the present invention.

In the context of the present invention, the term 'comprising' as used herein is understood as to have the meaning of 'including' or 'containing', which means that in addition to the explicitly mentioned element further elements are possibly present.

In a preferred embodiment of the present invention, the term 'comprising' as used herein is also understood to mean 'consisting of' thereby excluding the presence of other elements besides the explicitly mentioned element.

In a furthermore preferred embodiment, the term 'comprising' as used herein is also understood to mean 'consisting essentially of' thereby excluding the presence of other elements providing a significant contribution to the disclosed teaching besides the explicitly mentioned element.

Further preferred embodiments of the present invention are the subject-matter of the subclaims.

The invention will now be described in some more detail by way of the non-limiting examples and a FIGURE.

The sequence protocol shows:
SEQ ID NO: 1: the amino acid consensus sequence of the N-terminal tail domain of the CENH3 (part A),
SEQ ID NO: 2: the amino acid consensus sequence of the N-terminal tail domain of the CENH3 (part B),
SEQ ID NO: 3: the amino acid consensus sequence of the αN-helix of the CENH3,
SEQ ID NO: 4: the amino acid consensus sequence of the α1-helix of the CENH3,
SEQ ID NO: 5: the amino acid consensus sequence of the loop1 of the CENH3,
SEQ ID NO: 6: the amino acid consensus sequence of the α2-helix of the CENH3,
SEQ ID NO: 7: the amino acid consensus sequence of the loop2 of the CENH3,
SEQ ID NO: 8: the amino acid consensus sequence of the α3-helix of the CENH3,
SEQ ID NO: 9: the amino acid consensus sequence of the C-terminal domain of the CENH3,
SEQ ID NO: 10: the nucleotide sequence of the wildtype coding sequence (cDNA) of *A. thaliana* CENH3,
SEQ ID NO: 11: the amino acid sequence of the wildtype *A. thaliana* CENH3,
SEQ ID NO: 12: the nucleotide sequence of the wildtype genomic sequence (genomic DNA) of *B. napus* CENH3,
SEQ ID NO: 13: the nucleotide sequence of the wildtype coding sequence (cDNA) of *B. napus* CENH3,
SEQ ID NO: 14: the amino acid sequence of the wildtype *B. napus* CENH3,
SEQ ID NO: 15: the nucleotide sequence of the wildtype genomic sequence (genomic DNA) of *S. bicolor* CENH3,
SEQ ID NO: 16: the nucleotide sequence of the wildtype coding sequence (cDNA) of *S. bicolor* CENH3, SEQ ID NO: 17: the amino acid sequence of the wildtype *S. bicolor* CENH3, SEQ ID NO: 18: the nucleotide sequence of the wildtype genomic sequence (genomic DNA) of *Z. mays* CENH3, SEQ ID NO: 19: the nucleotide sequence of the wildtype coding sequence (cDNA) of *Z. mays* CENH3, SEQ ID NO: 20: the amino acid sequence of the wildtype *Z. mays* CENH3, SEQ ID NO: 21: the nucleotide sequence of the wildtype genomic sequence (genomic DNA) of *B. vulgaris* CENH3, SEQ ID NO: 22: the nucleotide sequence of the wildtype coding sequence (cDNA) of *B. vulgaris* CENH3, SEQ ID NO: 23: the amino acid sequence of the wildtype *B. vulgaris* CENH3, and SEQ ID NO: 24: the nucleotide sequence of the genomic sequence (genomic DNA) of *Z. mays* CENH3-Mu-mutation.

The FIGURE shows an alignment of the amino acid sequences of *Arabidopsis thaliana* (first row), *Beta vulgaris* (second row), *Brassica napus* (third row), *Zea mays* (fourth row), *Sorghum bicolor* (fifth row) as well as a diagram showing the level of conservation over these five plant species.

EXAMPLES

Identification of CENH3 Mutants

For the identification of mutations within the gene of CENH3 which cause an alteration of the amino acid sequence of the translated CENH3, wherein the alteration is able to confer the biological activity of a haploid inducer to a plant, all segments of the CENH3 gene has been investigated with respect to suitable mutations, even if Ravi und Chan 2010 highlighted only the particular importance of the N terminal domain. First own investigation on mutants in other segments like α2-helix (not yet published) gave indications that in addition the modification of other segments can result in a destabilization of the CENH3 binding capacities to DNA.

In order to find mutant CENH3 genes in different plants species Tilling populations having high mutation rates have generated for corn (*Zea mays*), rape seed (*Brassica napus*), sorghum (*Sorghum bicolor*) and sugar beet (*Beta vulgaris*) and have been screened for CENH3 mutations. For that, after development of amplicons covering all exons of the CENH3 genes 1000-10000 plants per plant species have been analyzed by means of Sanger's sequencing method. In addition, M2 sugar beet plants have been tested for mutations using specific PCR. Furthermore, the affect of the identified mutation within the CENH3 gene on the primary and secondary structure of the encoded protein have been evaluated using inter alia the software Prof (Rost, B. and Sander, C. (1994a). Combining evolutionary information and neural networks to predict protein secondary structure. Proteins, 19(1), 55-72. Rost, B. and Sander, C. (1994b). Conservation and prediction of solvent accessibility in protein families. Proteins, 20(3), 216-26. Rost, B., Casadio, R., Fariselli, P., and Sander, C. (1995). Transmembrane helices predicted at 95% accuracy. Protein Sci, 4(3), 521-33). Tables 9 to 12 show the identified mutations in *B. napus, Z. mays, S. bicolor* and *B. vulgaris*, respectively, which are separated in mutations causing a splicing error and in mutations causing an amino acid substitution. A mutation within a splicing site is of particular interest. Such mutation(s) can cause a malfunctioning splicing site (splicing error), which then results in an increased cellular translational production of non-fully functional CENH3 protein, which shows e.g. an impaired stability, a reduced binding affinity to DNA, a changed geometric shape of the protein, preferably a changed secondary or tertiary structure, or a disordered protein folding compared to the fully functional wildtype CENH3 protein. Plants having a genome which was heterozygous for such mutation(s) were viable.

TABLE 9 mutation of the CENH3 derived from *Brassica napus* (aa: amino acid; nd: not determined, y: yes, n: no). Amino acid substitution is given as X#Y, i.e. amino acid X (one letter code) is substituted for amino acid Y at position #.

| mutation identifier (*Brassica napus*) | codon wildtype | codon mutant | mutation | chance in secondary structure |
|---|---|---|---|---|
| BN_CenH3_01 | | | splicing error after aa at position 18 | nd |
| BN_CenH3_02 | | | splicing error after aa at position 33 | nd |
| BN_CenH3_03 | | | splicing error after aa at position 37 | nd |
| BN_CenH3_04 | | | splicing error after aa at position 37 | nd |
| BN_CenH3_05 | | | splicing error after aa at position 163 | nd |
| BN_CenH3_06 | tcc | ttc | S9F | y |
| BN_CenH3_07 | cga | caa | R16Q | y |
| BN_CenH3_08 | tcg | ttg | S24L | y |
| BN_CenH3_09 | gaa | aaa | E29K | n |
| BN_CenH3_10 | ggt | gat | G30D | n |
| BN_CenH3_11 | gcg | acg | A33T | n |
| BN_CenH3_12 | ccg | ctg | P35L | y |
| BN_CenH3_13 | agc | aac | S41N | n |
| BN_CenH3_14 | gga | gaa | G43E | y |
| BN_CenH3_15 | cct | tct | P50S | n |
| BN_CenH3_16 | cca | cta | P55L | n |
| BN_CenH3_17 | ggt | gat | G57D | n |
| BN_CenH3_18 | gga | gaa | G61E | y |
| BN_CenH3_19 | cga | caa | R65Q | y |
| BN_CenH3_20 | cga | tga | R65stop | n |
| BN_CenH3_21 | cct | tct | P71S | y |
| BN_CenH3_22 | gcc | acc | A105T | y |
| BN_CenH3_23 | cga | caa | R110Q | y |
| BN_CenH3_25 | agt | aat | S114N | y |
| BN_CenH3_26 | cct | tct | P121S | n |
| BN_CenH3_27 | tgg | tga | W127stop | n |
| BN_CenH3_28 | ctt | ttt | L132F | y |
| BN_CenH3_29 | gcg | acg | A138T | n |
| BN_CenH3_30 | tgc | tac | C153Y | y |
| BN_CenH3_31 | gct | gtt | A154V | y |
| BN_CenH3_32 | cgt | cat | R159H | n |
| BN_CenH3_33 | gtt | att | V160I | n |
| BN_CenH3_34 | gat | aat | D166N | n |
| BN_CenH3_35 | gag | aag | E168K | n |
| BN_CenH3_36 | cgt | cat | R172H | n |
| BN_CenH3_37 | ctt | ttt | L173F | n |
| BN_CenH3_38 | gga | gaa | G174E | y |
| BN_CenH3_39 | aga | aaa | R178K | n |

TABLE 10 mutation of the CENH3 derived from *Zea mays* (aa: amino acid; nd: not determined, y: yes, n: no). Amino acid substitution is given as X#Y, i.e. amino acid X (one letter code) is substituted for amino acid Y at position #.

| mutation identifier (*Zea mays*) | codon wildtype | codon mutant | mutation | chance in secondary structure |
|---|---|---|---|---|
| ZM_CenH3_01 | | | splicing error after aa at position 89 | nd |
| ZM_CenH3_02 | | | splicing error after aa at position 115 | nd |

TABLE 10-continued mutation of the CENH3 derived from *Zea mays* (aa: amino acid; nd: not determined, y: yes, n: no). Amino acid substitution is given as X#Y, i.e. amino acid X (one letter code) is substituted for amino acid Y at position #.

| mutation identifier (*Zea mays*) | codon wildtype | codon mutant | mutation | chance in secondary structure |
|---|---|---|---|---|
| ZM_CenH3_03 | | | splicing error after aa at position 141 | nd |
| ZM_CenH3_04 | gcg | acg | A32T | nd |
| ZM_CenH3_05 | gaa | aaa | E35K | nd |
| ZM_CenH3_06 | cca | tca | P56S | nd |
| ZM_CenH3_07 | gca | aca | A107T | nd |
| ZM_CenH3_08 | caa | taa | Q114stop | nd |
| ZM_CenH3_09 | gga | gaa | G152E | nd |
| ZM_CenH3_10 | cgt | cat | R155H | nd |
| ZM_CenH3_11 | gtg | atg | V89M | nd |
| ZM_CenH3_12 | aca | ata | T139I | nd |

TABLE 11 mutation of the CENH3 derived from *Sorghum bicolor* (aa: amino acid; nd: not determined, y: yes, n: no). Amino acid substitution is given as X#Y, i.e. amino acid X (one letter code) is substituted for amino acid Y at position #.

| mutation identifier (*S. bicolor*) | codon wildtype | codon mutant | mutation | chance in secondary structure |
|---|---|---|---|---|
| SB_CenH3_01 | | | splicing error after aa at position 26 | nd |
| SB_CenH3_02 | gca | gta | A62V | nd |
| SB_CenH3_03 | act | agt | T64S | nd |
| SB_CenH3_04 | gca | gta | A95V | nd |
| SB_CenH3_05 | gca | aca | A25T | nd |
| SB_CenH3_06 | tcg | ttg | S157L | nd |

TABLE 12 mutation of the CENH3 derived from *Beta vulgaris* (nd: not determined, y: yes, n: no). Amino acid substitution is given as X#Y, i.e. amino acid X (one letter code) is substituted for amino acid Y at position #.

| mutation identifier (*Beta vulgaris*) | codon wildtype | codon mutant | mutation | chance in secondary structure |
|---|---|---|---|---|
| Bv_CENH3_01 | gat | aat | D46N | nd |
| Bv_CENH3_02 | gat | ggt | D46G | nd |
| Bv_CENH3_03 | aga | aaa | A2K | nd |
| Bv_CENH3_04 | ctg | cag | L106Q | nd |
| Bv_CENH3_05 | ctt | cct | L109P | nd |
| Bv_CENH3_06 | caa | cta | Q110L | nd |

Beside mutations of splicing sites and point mutations causing amino acid substitutions within the amino acid sequence of CENH3 protein a corn mutant (called Mu-mutant) has been identified that contains a transposon insertion within the 5' untranslated region of the CENH3 gene (see SEQ ID NO: 24). This mutation causes an extension of the N terminal tail domain. Thus, the effect of this mutation on CENH3 is very similar to the mutation described by Ravi & Chan (2010) except that the mutation is non-transgenic.

Testing of CENH3 Mutants

To evaluate the biological activity of a haploid inducer in the identified mutants and to test the maternal and paternal performance of haploid induction the mutant plants have to be crossed with another tester plant of the same species (carrying wildtype form of CENH3) that can be used as ovule parent or pollen parent, respectively. Putative haploid progeny from this cross can be determined quickly if the used tester lines carry a recessive non-CENH3 mutation. So, the haploid plants show the recessive phenotype. For example, in corn the manifestation of the mutation glossy (Mutants of maize, Neuffer, M G et al. 1997. Cold Spring Harbor Laboratory, New York) can be used.

Cytogenetic analyses of mitose and meiose with the inductors give indications for suitability of mutants as haploid inducers. The homozygosity is determined by use of molecular markers, polymorph for tester and potential inductor. Haploidy as such is tested cytogenetically.

In crossings with the tester plants the TILLING plants with mutated endogenous CENH3 gene as described above yield at least 0.4% haploid progeny. Frequently but not always, the induction rate was higher if the tester was used as female parent in the cross.

For example, in *Brassica napus* the mutations that base on amino acid substitutions in the N-terminal tail domain result in induction rates of at least 0.5% and partly up to more than 2%. Thereby, the locations of mutations are not specific to a certain region in this domain but rather distributed over the entire domain. The N-terminal tail domain in *Brassica napus* reaches from amino acid position 1 to 84. Mutations conferring the biological activity of a haploid inducer can be found for instances in positions 9, 16, 24, 29, 30, 33, 41, 43, 50, 55, 57 and 61, whereby not all of these mutations lead necessarily to a chance in secondary structure of the protein (calculated in silico). Comparable results have been achieved for the more conserved histone fold domain containing the three helices and the two loops. Even though over the entire histone fold domain suitable mutations can be found specifically amino acid substitutions in the α2-helix, the CATD domain and the loop2 yielded on average significantly higher induction rates. Due to these observations on the N-terminal tail domain and the histone fold domain, it can be assumed that also other not tested positions and other not tested amino substitutions will confer the same or even an improved haploid inductivity. Further, another kind of modification of the endogenous CENH3 gene is the substitution of nucleotides in splicing sites what consequently leads to splicing errors. Such mutations are also suitable to confer the biological activity of a haploid inducer. The observed induction rates showed at least 0.5% haploid progeny. Even here it can be assumed that also other not tested splicing sites will confer the same or even an improved haploid inductivity.

For example, in *Zea mays* the mutations that base on amino acid substitutions in the N-terminal tail domain result in induction rates of at least 0.4%. Thereby, the locations of mutations are not specific to a certain region in this domain but rather distributed over the entire domain. The N-terminal tail domain in *Zea mays* reaches from amino acid position 1 to 62. Mutations conferring the biological activity of a haploid inducer can be found for instances in positions 32, 35 and 56. Comparable results have been achieved for the more conserved histone fold domain containing the three helices and the two loops. Due to these observations on the N-terminal tail domain and the histone fold domain, it can be assumed that also other not tested positions and other not tested amino substitutions will confer the same or even an improved haploid inductivity. Further, another kind of modification of the endogenous CENH3 gene is the substitution of nucleotides in splicing sites what consequently leads to splicing errors. Such mutations are also suitable to confer the biological activity of a haploid inducer. The observed induction rates showed at least 0.4% haploid progeny. Even here it can be assumed that also other not tested splicing sites will confer the same or even an improved haploid inductivity.

In addition the Mu-mutant containing a transposon insertion within the 5' untranslated region of the CENH3 gene (SEQ ID NO: 24) has been tested for biological activity of a haploid inducer. This non-transgenic mutation causes an induction rate of more than 1.0%.

Moreover, the results of crossing across different crops demonstrate that identified and indicated mutations could be functional even in further plant species. Therefore mutations could be introduced into other plant species by techniques like TILLING, Mutagenesis or genome editing (e.g. CRISPR/Cas, TALENs, Zinc Finger nucleases etc.). Moreover, the biological activity and efficiency of a haploid inducer could be further improved by combining different identified mutations in one plant and/or modifying the genetic background of the haploid inducer. The combination of different mutations could be achieved efficiently by genome editing, or the mutant haploid inducer is mutagenized for a second time.

The invention claimed is:

1. A plant having a biological activity of a haploid inducer and comprising a polynucleotide which comprises a nucleotide sequence encoding a centromeric histone H3 (CENH3) protein, wherein the nucleotide sequence comprises at least one introduced mutation that alters the amino acid sequence of the CENH3 protein in an N-terminal domain and confers the biological activity of a haploid inducer to the CENH3 protein,
wherein
i. the amino acid arginine at position 3 of SEQ ID NO: 1 is substituted for lysine,
ii. the amino acid arginine at position 3 of SEQ ID NO: 20 is substituted for glutamine,
iii. the amino acid arginine at position 10 of SEQ ID NO: 1 is substituted for phenylalanine,
iv. the amino acid serine at position 9 of SEQ ID NO: 14 is substituted for phenylalanine,
v. the amino acid arginine at position 16 of SEQ ID NO: 14 is substituted for glutamine,
vi. the amino acid proline at position 16 of SEQ ID NO: 20 is substituted for leucine,
vii. the amino acid serine at position 24 of SEQ ID NO: 14 is substituted for leucine,
viii. the amino acid alanine at position 25 of SEQ ID NO: 17 is substituted for threonine,
ix. the amino acid glutamic acid at position 29 of SEQ ID NO: 14 is substituted for lysine,
x. the amino acid glycine at position 30 of SEQ ID NO: 14 is substituted for aspartic acid,
xi. the amino acid alanine at position 33 of SEQ ID NO: 14 or at position 32 of SEQ ID NO: 20 is substituted for threonine,
xii. the amino acid proline at position 35 of SEQ ID NO: 14 is substituted for leucine,
xiii. the amino acid glutamic acid at position 35 of SEQ ID NO: 20 is substituted for lysine,
xiv. the amino acid serine at position 41 of SEQ ID NO: 14 is substituted for asparagine,
xv. the amino acid glycine at position 42 of SEQ ID NO: 17 is substituted for glutamic acid,
xvi. the amino acid glycine at position 43 of SEQ ID NO: 14 is substituted for glutamic acid,
xvii. the amino acid proline at position 50 of SEQ ID NO: 14 is substituted for serine,
xviii. the amino acid proline at position 55 of SEQ ID NO: 14 is substituted for leucine,
xix. the amino acid glutamic acid at position 55 of SEQ ID NO: 17 is substituted for lysine,
xx. the amino acid glycine at position 57 of SEQ ID NO: 14 is substituted for aspartic acid,
xxi. the amino acid glycine at position 61 of SEQ ID NO: 14 is substituted for glutamic acid,
xxii. the amino acid arginine at position 65 of SEQ ID NO: 14 is substituted for glutamine,
xxiii. the amino acid arginine at position 65 of SEQ ID NO: 14 is substituted for stop signal,
xxiv. the amino acid proline at position 71 of SEQ ID NO: 14 is substituted for serine,
xxv. the amino acid aspartic acid at position 46 of SEQ ID NO: 23 is substituted for asparagine or glycine,
xxvi. the amino acid lysine at position 7 of SEQ ID NO: 2 is substituted for serine,
xxvii. the amino acid proline at position 56 of SEQ ID NO: 20 is substituted for serine,
xxviii. the amino acid proline at position 14 of SEQ ID NO: 2 is substituted for valine, or
xxix. the amino acid alanine at position 62 of SEQ ID NO: 17 is substituted for valine.

2. The plant according to claim 1, wherein crossing between the plant and a wildtype plant or a plant expressing wildtype CENH3 protein yields at least 0.1% haploid progeny.

3. The plant according to claim 1, wherein the polynucleotide comprising the at least one mutation is an endogenous gene or a transgene.

4. A part of the plant according to claim 1, wherein the part is a leaf, a stem, a root, an emerged radicle, a flower, a petal, a fruit, pollen, a pollen tube, an anther filament, an ovule, an embryo sac, an egg cell, an ovary, a zygote, an embryo, a hypocotyl section, an apical meristem, a vascular bundle, a pericycle, a seed, a cutting, a cell culture, or a tissue culture.

5. The part of the plant according to claim 4, wherein the part is a shoot, a vegetative organ, a root, a flower, a floral organ, a seed, a fruit, an ovule, an embryo, a plant tissue or a cell.

6. A method of generating a haploid plant, comprising the steps of:
a) crossing the plant according to claim 1 to a plant expressing wildtype CENH3 protein; and
b) identifying the haploid progeny plant generated from the crossing step.

7. A method of generating a double haploid plant, comprising the steps of:
a) crossing the plant according to claim 1 to a plant expressing wildtype CENH3 protein;
b) identifying a haploid progeny plant generated from the crossing step; and
c) converting the haploid progeny plant into a double haploid plant.

8. The method of claim 7, wherein in step c) the haploid progeny plant is converted into a double haploid plant via colchicine treatment or via spontaneous chromosome doubling.

9. A method of facilitating a cytoplasm exchange, comprising the steps of:
a) crossing the plant according to claim 1 as an ovule parent with a plant expressing wildtype CENH3 protein as a pollen parent; and
b) obtaining a haploid progeny plant comprising the chromosomes of the pollen parent and the cytoplasm of the ovule parent.

10. A method of generating a plant according to claim 1, comprising the steps of:
i) subjecting seeds of a plant to a sufficient amount of a mutagen, to obtain M1 plants,
ii) allowing sufficient production of fertile M2 plants,
iii) isolating genomic DNA of M2 plants, and
iv) selecting individuals possessing at least one mutation in a polynucleotide comprising a nucleotide sequence encoding a centromeric histone H3 (CENH3) protein, wherein the at least one mutation causes an alteration of the amino acid sequence of the CENH3 protein in the N-terminal domain of CENH3.

11. The method of claim 10, wherein the mutagen is ethylmethane sulfonate.

* * * * *